United States Patent [19]

Burgert et al.

[11] Patent Number: 5,629,377
[45] Date of Patent: May 13, 1997

[54] WATER ABSORBENT RESIN PARTICLES OF CROSSLINKED CARBOXYL CONTAINING POLYMERS AND METHOD OF PREPARATION

[75] Inventors: Josef H. Burgert, Achern, Germany; Stephen B. Christensen, Midland, Mich.; Herbert A. Gartner, Baden-Baden, Germany; Fredric L. Buchholz, Midland, Mich.; Thomas C. Johnson, Midland, Mich.; Andrew T. Graham, Midland, Mich.

[73] Assignee: The Dow Chemical Company, Midland, Mich.

[21] Appl. No.: 505,181

[22] PCT Filed: Mar. 8, 1994

[86] PCT No.: PCT/US94/02445

§ 371 Date: Aug. 11, 1995

§ 102(e) Date: Aug. 11, 1995

[87] PCT Pub. No.: WO94/20547

PCT Pub. Date: Sep. 15, 1994

[30] Foreign Application Priority Data

Mar. 10, 1993 [GB] United Kingdom .................. 9304857

[51] Int. Cl.$^6$ .................................................. C08L 31/02
[52] U.S. Cl. .................. 524/832; 525/329.5; 525/329.7; 525/330.3; 525/367; 524/827
[58] Field of Search ........................ 524/832, 877; 525/329.1, 329.5, 329.7, 330.3, 367

[56] References Cited

U.S. PATENT DOCUMENTS

| Re. 32,649 | 4/1988 | Brandt et al. | 604/368 |
| 4,295,987 | 10/1981 | Parks | 252/194 |
| 4,415,388 | 11/1983 | Korpman | 156/78 |
| 4,610,678 | 9/1986 | Weisman et al. | 604/368 |
| 4,654,039 | 3/1987 | Brandt et al. | 604/368 |

FOREIGN PATENT DOCUMENTS

| 0205674 | 12/1986 | European Pat. Off. . |
| 0317106 | 10/1988 | European Pat. Off. . |
| 0509708 | 10/1992 | European Pat. Off. . |
| 2119384 | 11/1983 | United Kingdom . |
| 2155020 | 9/1985 | United Kingdom . |
| 9015829 | 12/1990 | WIPO . |
| 9321237 | 10/1993 | WIPO . |

OTHER PUBLICATIONS

Derwent Abstract, JP 55082104, Union Carbide Corp., Jun. 20, 1980.

Primary Examiner—Jeffrey T. Smith

[57] ABSTRACT

A water-absorbent resin particles that exhibits a centrifuged absorption capacity of 26 g/g or greater, an absorption under load of 24 g/g or greater at 0.6 psi load. Other aspects of the invention are processes for the preparation of such water-absorbent resin particles which comprise the inclusion of chlorine or bromine containing oxidizing agent followed by the heat-treatment to produce particles with superior centrifuged absorption capacity in combination with high absorption under load at high load, and acceptable levels of residuals. These water-absorbent resin particles provide superior performance when incorporated into absorbent structures.

20 Claims, 1 Drawing Sheet

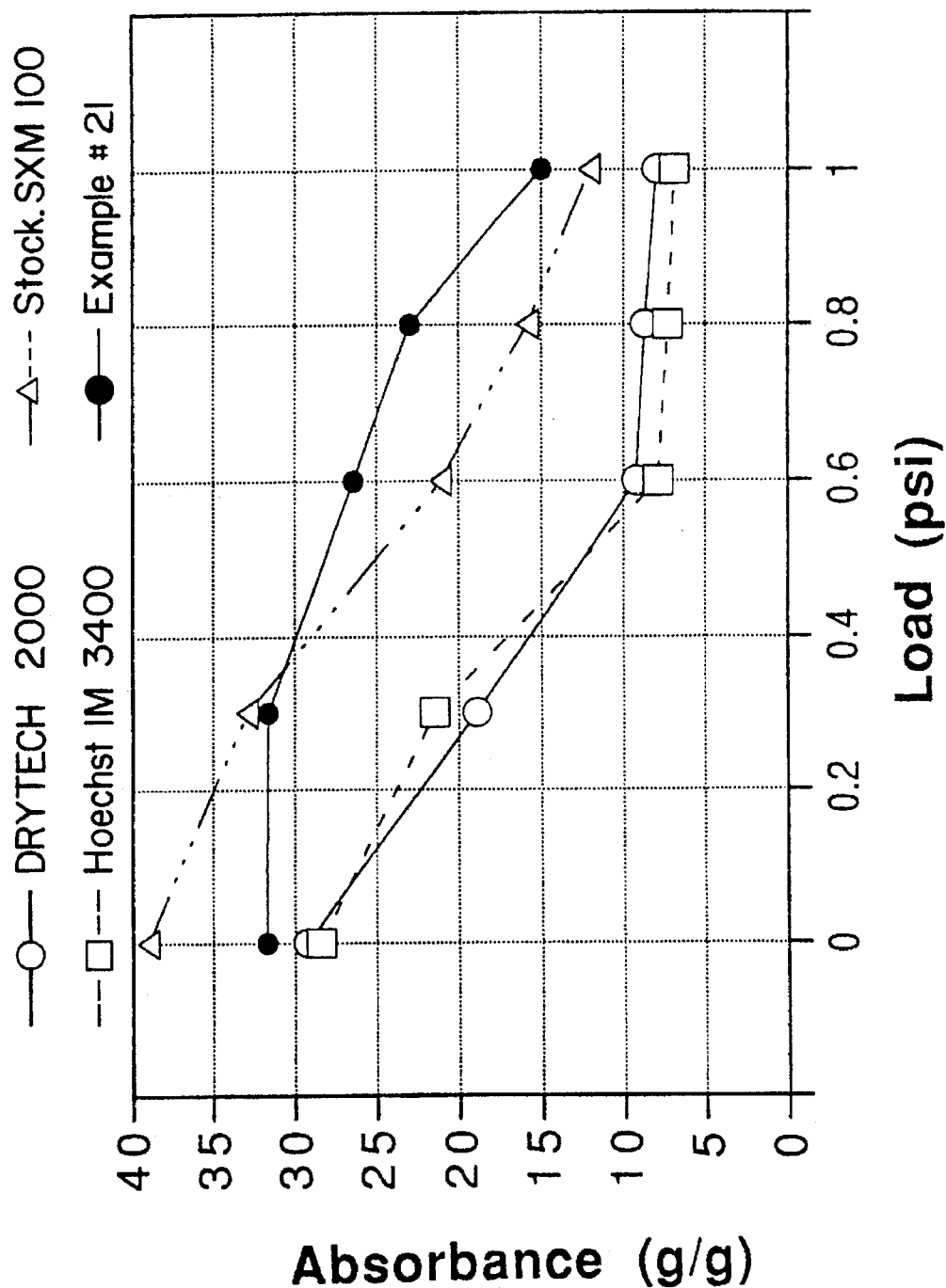
Figure

WATER ABSORBENT RESIN PARTICLES OF CROSSLINKED CARBOXYL CONTAINING POLYMERS AND METHOD OF PREPARATION

This invention relates to water-absorbent particles of crosslinked carboxyl-containing polymers which have both high absorption capacity and high absorption capacity under load, and methods for preparing such particles and absorbent structures incorporating the particles.

Water-absorbent resin particles, also referred to as aqueous fluid absorbent polymers or superabsorbent polymers, are primarily used in personal care products which absorb body fluids, for example, baby diapers, adult incontinence products and feminine hygiene products. In such applications, water-absorbent resin particles are incorporated into absorbent structures which contain synthetic and/or natural fiber or paper based, woven and nonwoven structures, or toughened masses of fibers, such as fluff pads. The materials used in such structures can quickly absorb aqueous fluids and distribute them over the whole absorbent structure. The structures, in the absence of water-absorbent resin particles, have limited absorption capacity, are bulky due to the large amount of material needed to provide acceptable absorption capacity, and do not retain fluid under pressure. A means for improving the absorbency and fluid retention characteristics of such absorbent structures is to incorporate water-absorbent resin particles which imbibe fluids to form a swollen hydrogel material.

The water-absorbent resin particles quickly absorb fluids and retain such fluids to prevent leakage and give the absorbent structure a "dry feel" even when wetted. See U.S. Pat. No. 4,610,678 for examples of such resins. See also Brandt U.S. Pat. Nos. 4,654,039 and Re. 32,649, which discloses a process for the preparation of water-absorbent resins and the use of known crosslinking agents for such resins, and also Parks U.S. Pat. No. 4,295,987 and Japan Patent No. 55-82104. A variation of the basic process is taught in GB Patent No. 2,119,384, which discloses a post polymerization surface crosslinking process in which the previously polymerized absorbent resin powder is mixed with crosslinkers, preferably polyalcohols, a solvent and water, to coat the resin surface and heated to temperatures in the range of 90° C. to 300° C. to crosslink the surface. Commonly assigned Great Britain Patent Application No. 9208449.0 discloses water-absorbent resin particles comprising polymers containing carboxyl moieties which are crosslinked using $C_{2-10}$ polyhydric hydrocarbons which are ethoxylated with from 2 to 8 ethylene oxide units per hydroxyl moiety of the ethylene oxide chain wherein the hydroxyl moiety at the end of each chain is esterified with a $C_{2-10}$ unsaturated carboxylic acid or ester thereof. In a preferred embodiment, the water-absorbent resin particles are subjected to a heat-treatment after drying and sizing the particles.

To reduce the amount of absorbent resin required it is desirable for the absorption capacity of resin to be as high as possible. This is normally accomplished by adjustment of the crosslinker level within the resin particle. An increase in absorption capacity, however, is generally accompanied by a decrease in the ability of the resin particles to absorb liquid under an applied load. This absorption under load (AUL) is important to the performance of the resin, with higher values being preferred. Most commercially available resin particles demonstrate good AUL at low loads, such as 2.1 kPa (0.3 pound per square inch) (psi where 1 psi=6894.76 Pa). Unfortunately, these resins demonstrate a dramatic drop in absorption capacity as the load is increased to higher levels, such as 4.1 kPa (0.6 psi), 5.5 kPa (0.8 psi) or 6.9 kPa (1.0 psi). What is needed is a water-absorbent resin particle which retains most of its absorption capacity as the load increases.

A further problem with commercially available water-absorbent resin particles is the presence of monomers or low molecular weight polymer which may leach out. This monomer or low weight polymer represents additional raw material cost which provides at best a possible marginal benefit, if any, to the resin properties. It is desirable to reduce the residual monomer and leachable, low molecular weight polymer of the resin without significantly reducing the absorption capacity or absorption capacity under load.

Therefore, it would be desirable to have available water-absorbent resin particles which have high absorption capacity, high absorption under load, and low residual monomer level, as well as processes for the preparation of such particles.

This invention relates to a water-absorbent resin particle having a centrifuged absorption capacity of 26 g/g or greater and an absorption under load of 24 g/g or greater at 4.1 kPa (0.6 psi) load, the particle comprising from 80 to 99.9 weight percent of a crosslinked carboxyl-containing polymer prepared by polymerizing a polymerization mixture which comprises:

(a) from 70 to 99.9 weight percent of one or more ethylenically unsaturated carboxyl containing monomers, (b) from 0.1 to 5 weight percent of one or more crosslinking agents, and (c) from 0 to 25 weight percent of one or more monomers copolymerizable with the carboxyl containing monomer, wherein the weight percentages of the polymerization mixture are based on the total weight of (a), (b) and (c).

(d) from 10 to 2000 ppm by weight of a chlorine or bromine containing oxidizing agent, wherein the weight percentages and ppm of the polymerization mixture are based on the total weight of (a), (b) and (c), wherein the oxidizing agent has been substantially uniformly distributed within the resin particle prior to heat-treatment, and wherein the resin particle has been heated at a temperature of from 170° C. to 250° C. for from 1 to 60 minutes.

Preferred embodiments of the water absorbent resin particle are those wherein (i) the resin particle has an absorption under load of 17 g/g or greater at 5.5 kPa (0.8 psi), load, or (ii) the resin particle has an absorption under load of 14 g/g or greater at 6.9 kPa (1 psi) load, or (iii) the resin particle has an absorption under load of 22 g/g or greater at 5.5 kPa (0.8 psi), load and the resin particle has an absorption under load of 20 g/g or greater at.6.9 kPa (1 psi), load, or (iv) the resin particle has a centrifuged absorption capacity of 30 g/g or greater, or (v) the resin particle has a centrifuged absorption capacity of 30 g/g or greater and an absorption under load of 17 g/g or greater at 5.5 kPa (0.8 psi) load, or (vi) the resin particle has a centrifuged absorption capacity of 30 g/g or greater and an absorption under load of 14 g/g or greater at 6.9 kPa (1 psi) load, or (vii) the resin particle has a centrifuged absorption capacity of 30 g/g or greater and an absorption under load of 22 g/g or greater at 5.5 kPa (0.8 psi) load, or (viii) the resin particle has a centrifuged absorption capacity of 37 g/g or greater and an absorption under load of 17 g/g or greater at 5.5 kPa (0.8 psi) load.

Another aspect of the invention is a process for the preparation of water-absorbent resin particles which comprises:

(I) polymerizing a polymerization mixture comprising:
  (a) from 70 to 99.9 weight percent of one or more ethylenically unsaturated carboxyl containing monomers,
  (b) from 0.1 to 5 weight percent of one or more crosslinking agents,
  (c) from 0 to 25 weight percent of one or more comonomers copolymerizable with the carboxyl containing monomer,
  (d) an aqueous or nonaqueous polymerization medium, and
  (e) from 10 to 2000 ppm by weight of a chlorine or bromine containing oxidizing agent to form a crosslinked hydrogel wherein the weight percentages and ppm are based on the total weight of (a), (b) and (c);
(II) optionally, comminuting the hydrogel to particles;
(III) drying the hydrogel by substantially removing the polymerization medium to form resin;
(IV) optionally, comminuting the resin to particles;
(V) heating the particles at a temperature of from 170° C. to 250° C. for from 1 to 60 minutes.

In another embodiment this aspect of the invention is a process for the preparation of water-absorbent resin particles which comprises:

(I) polymerizing a polymerization mixture comprising:
  (a) from 70 to 99.9 weight percent of one or more ethylenically unsaturated carboxyl containing monomers,
  (b) from 0.1 to 5 weight percent of one or more crosslinking agents,
  (c) from 0 to 25 weight percent of one or more comonomers copolymerizable with the carboxyl containing monomer, and
  (d) an aqueous or nonaqueous polymerization medium to form a crosslinked hydrogel wherein the weight percentages are based on the total weight of (a), (b) and (c);
(II) optionally, comminuting the hydrogel to particles;
(III) applying to the hydrogel a chlorine or bromine containing oxidizing agent dispersed or dissolved in a liquid so that there is substantially uniformly distributed through the hydrogel particles from 10 to 2000 ppm by weight, based on the weight of (a), (b) and (c), of the chlorine or bromine containing oxidizing agent
(IV) drying the hydrogel by substantially removing the polymerization medium and the liquid to form resin;
(V) optionally, comminuting the resin particles;
(VI) heating the particles at a temperature of from 170° C. to 250° C. for from 1 to 60 minutes.

In yet another embodiment the invention is an absorbent structure comprising a woven or nonwoven structure of synthetic or natural fibers and the water-absorbent resin particles of this invention or the particles produced by the process of this invention.

DESCRIPTION OF THE DRAWINGS

FIG. 1 is a plot of absorption under load versus pressure in kPa after 60 minutes absorption of several commercially available resins, DRYTECH™ 2000 water-absorbent resin (trademark of The Dow Chemical Company), Hoechst Celanese SANWIT IM™ 3400 water-absorbent resin, Stockheusen FAVOR SXM™ 100 water-absorbent resin, and Example 21 of the current invention.

The water-absorbent resin particles (hereinafter "resin particles") of this invention demonstrate high absorption capacity, high absorption under load, and low residual monomer levels. The particles demonstrate a lower loss of absorption capacity as the load level increases as compared to commercially available water-absorbent particles. The resin particles comprise crosslinked carboxyl-containing polymers prepared with an oxidizing agent, typically a chlorine or bromine containing oxidizing agent (which may be referred to as the oxidizer of the invention or just oxidizer), that are heated in the substantially dry state to achieve the desired properties. The substantially dry state is that state achieved in the drying step of the processes of this invention where polymerization medium and any liquid dispersing medium is substantially removed to prepare the hydrogel for the optional comminution step. In the substantially dry state the residual moisture content may be as high as 20 percent by weight. The post-polymerization heating step in the process for the preparation of the water-absorbent resin particles allows variation of the process to achieve a desired mix of properties, that is absorption under load, absorption capacity and residual monomer level.

The unique properties of the resin of the current invention result from this combination of heat-treatment and a substantially uniform distribution of the oxidizing agent prior to heat-treatment. Heat-treatment of resin alone without inclusion of the oxidizing agent has been shown in U.S. Pat. No. 5,206,205 to provide a beneficial increase in the absorption under load (AUL) of an absorbent resin, particularly the AUL at higher pressures. However, this heat-treatment also typically reduces the centrifuged absorption capacity of the resin, often to a level that is unacceptably low. Thus, prior to this invention it was difficult to achieve a resin that had both a high centrifuged absorption capacity and a high AUL. Uniform inclusion an oxidizing agent in a resin prior to heat-treatment gives a higher post heat-treatment centrifuged absorption capacity than is obtainable without it. Thus, the processes of this invention produce a superabsorbent resin with both a high centrifuged absorption capacity and a high AUL.

The utilization of an oxidizing agent also has the effect of reducing the residual monomer content in the final heat-treated product compared with that observed when the resin is heat-treated without the oxidizing agent of this invention. The greater post heat-treatment centrifuged absorption capacity, in combination with high absorption under load, and a reduction in post heat-treatment residual monomer content are herein referred to collectively as the "chlorate effect." Although sodium chlorate is the preferred oxidizing agent for many reasons, the term "chlorate effect" is applicable to the result produced by the effective inclusion of any suitable oxidizing agent.

The polymers of the resin particles are derived from one or more ethylenically unsaturated carboxylic acids, ethylenically unsaturated carboxylic acid anhydrides or salts thereof. Additionally, the polymers may include comonomers known in the art for use in water-absorbent resin particles or for grafting onto the water-absorbent resins including comonomers such as an acrylamide, an acrylonitrile, a vinyl pyrrolidone, a vinyl sulphonic acid or a salt thereof, a cellulosic monomer, a modified cellulosic monomer, a polyvinyl alcohol or a starch hydrolyzate.

Preferable unsaturated carboxylic acid and carboxylic acid anhydride monomers include the acrylic acids typified by acrylic acid, methacrylic acid, ethacrylic acid, alpha-chloroacrylic acid, alpha-cyano acrylic acid, beta-methyl-acrylic acid (crotonic acid), alpha-phenyl acrylic acid, beta-acryloyloxy propionic acid, sorbic acid, alpha-chloro sorbic acid, angelic acid, cinnamic acid, p-chloro cinnamic acid, beta-styd acrylic acid (1-carboxy-4-phenyl butadiene-1,3), itaconic acid, citraconic acid, mesaconic acid, glutaconic acid, maleic acid, fumaric acid and maleic acid anhydride. More preferably the starting monomer is acrylic acid, methacrylic acid, or a salt thereof, with acrylic acid or a salt thereof being most preferred.

The use herein of the prefix "(meth)" with generic terms, such as, for example, "acrylic acid", or "acrylate" is meant to broaden the terms to include both acrylate and methacrylate species. Thus, the term "(meth)acrylic acid monomer" includes acrylic acid and methacrylic acid.

Incorporated into the resin are polyvinyl crosslinkers commonly known in the art for use in water-absorbent resin particles. Preferable compounds having at least two polymerizable double bonds include: di- or polyvinyl compounds such as divinyl benzene, divinyl toluene, divinyl xylene, divinyl ether, divinyl ketone and trivinyl benzene; di- or polyesters of unsaturated mono- or polycarboxylic acids with polyols, such as di- or tri-(meth)acrylic acid esters of polyols such as ethylene glycol, diethylene glycol, triethylene glycol, tetra ethylene glycol, propylene glycol, dipropylene glycol, tri propylene glycol, tetra propylene glycol, trimethylol propane, glycerin, polyoxyethylene glycols and polyoxypropylene glycols; unsaturated polyesters that can be obtained by reacting any of the above-mentioned polyols with an unsaturated acid such as maleic acid; di- or polyesters of unsaturated mono- or polycarboxylic acids with polyols derived from reaction of $C_2$–$C_{10}$ polyhydric alcohols with 2 to 8 $C_2$–$C_4$ alkylene oxide units per hydroxyl group, such as tri methylol propane hexaethoxyl triacrylate; di- or tri-(meth)acrylic acid esters that can be obtained by reacting polyepoxide with (meth)acrylic acid; bis(meth) acrylamides such as N,N-methylene-bisacrylamide; carbamyl esters that can be obtained by reacting polyisocyanates such as tolylene diisocyanate, hexamethylene diisocyanate, 4,4'-diphenyl methane diisocyanate and NCO-containing prepolymers obtained by reacting such diisocyanates with active hydrogen atom-containing compounds with hydroxyl group-containing monomers, such as di-(meth)acrylic acid carbamyl esters obtainable by reacting the above-mentioned diisocyanates with hydroxyethyl(meth)acrylate; di- or poly(meth)allyl ethers of polyols such as alkylene glycols, glycerol, polyalkylene glycols, polyoxyalkylene polyols and carbohydrates such as polyethylene glycol diallyl ether, allylated starch, and allylated cellulose; di- or poly-allyl esters of polycarboxylic acids, such as diallyl phthalate and diallyl adipate; and esters of unsaturated mono- or polycarboxylic acids with mono(meth)allyl ester of polyols, such as allyl methacrylate or (meth)acrylic acid ester of polyethylene glycol monoallyl ether.

Among the preferred classes of crosslinkers are bis(meth)-acrylamides; allyl(meth)acrylates; di- or poly-esters of (meth)acrylic acid with polyols such as diethylene glycol diacrylate, trimethylol propane triacrylate, and polyethylene glycol diacrylate; and di- or poly-esters of unsaturated mono- or poly-carboxylic acids with polyols derived from reaction of $C_1$–$C_{10}$ polyhydric alcohols with 2 to 8 $C_2$–$C_4$ alkylene oxide units per hydroxyl group, such as ethoxylated trimethylol propane triacrylate. More preferably the crosslinking agents correspond to Formula 1

$$R^1(-(R^2O)_n-C(O)R^3)_x \text{ Formula 1}$$

wherein:

$R^1$ is a straight- or branched-chain polyalkoxy radical with 1 to 10 carbon atoms, optionally substituted with one or more oxygen atoms in the backbone, having x valences;

$R_2$ is independently in each occurrence an alkylene group of 2 to 4 carbon atoms;

$R_3$ is independently in each occurrence a straight- or branched-chain alkenyl moiety with 2 to 10 carbon atoms;

n is a positive integer from 1 to 20;

x is a positive integer from 2 to 8.

In the most preferred embodiment the polyvinyl crosslinker corresponds to Formula 1 wherein $R^1$ is derived from trimethylolpropane, $R^2$ is ethylene ($CH_2CH_2$), $R^3$ is vinyl ($CH=CH_2$), n is an average of from 2 to 6, and x is 3. In particular the most preferred polyvinyl crosslinker is highly ethoxylated trimethylolpropane triacrylate, containing an average of about 15 to 16 ethoxyl groups per molecule of tri methylolpropane. Crosslinkers corresponding to Formula 1 are available from Craynor under the trademark Craynor and from Sartomer under the trademark Sartomer. Generally, the crosslinkers described by Formula 1 are found as a mixture of materials described by the formula and by-products resulting from the preparation process.

The non-vinyl crosslinkers of this invention are agents having at least two functional groups capable of reacting with the carboxyl groups of the polymer, such as glycerin, polyglycols, ethylene glycol, digylcidyl ether, and aliamines. Many examples of these agents are given in U.S. Pat. Nos. 4,666,983 and 4,734,478 which teach the application of such agents to the surface of absorbent resin powder followed by heating to crosslink surface chains and improve absorption capacity and absorption rate. Additional examples are given in U.S. Pat. No. 5,145,906 which teaches post-crosslinking with such agents. In the current invention, the non-vinyl crosslinkers are added homogeneously to the polymerization mixture at the start of the process. Preferred non-vinyl crosslinkers include hexane diamine, glycerin, ethylene glycol diglycidyl ether, ethylene glycol diacetate, polyethylene glycol 400, polyethylene glycol 600, and polyethylene glycol 1000. Most preferred non-vinyl crosslinkers include polyethylene glycol 400 and polyethylene glycol 600.

The dimodal crosslinkers of this invention are agents that have at least one polymerizable vinyl group and at least one functional group capable of reacting with carboxyl groups. To distinguish these from normal vinyl crosslinkers, we call them "dimodal crosslinkers," because they use two different modes of crosslinking. Possible dimodal crosslinkers include hydroxyethyl methacrylate, polyethylene glycol monomethacrylate, glycidyl methacrylate, and allyl glycidyl ether. Many examples of these type of agents are given in U.S. Pat. Nos. 4,962,172 and 5,147,956 which teach the manufacture of absorbent films and fibers by (1) the preparation of linear copolymers of acrylic acid and hydroxyl containing monomers, (2) forming solutions of these copolymers into the desired shapes, and (3) fixing the shape by heating the polymer to form ester crosslinks between the pendant hydroxyl and carboxyl groups. In the current invention the dimodal crosslinkers are added homogeneously to the polymerization mixture at the start of the process. Preferred dimodal crosslinkers include hydroxyethyl (meth) acrylate, polyethylene glycol 400 monomethacryl ate, glycidyl methacrylate. Most preferred dimodal crosslinkers include hydroxyethyl (meth)acrylate.

The total amount of all crosslinkers present is sufficient to provide a resin with good absorptive capacity, good absorption under load, and a low percent of extractable materials. Preferably the crosslinkers are present in an amount of 1,000 parts per million or more by weight based on the amount of the polymerizable monomer present, more preferably 2,000 parts per million or more and most preferably 4000 parts per million or greater. Preferably the crosslinkers are present in an amount of 50,000 parts per million or less by weight based upon the amount of the polymerizable monomer present, more preferably in amounts of 20,000 parts per million or less and most preferably 15,000 parts per million or less.

In those embodiments of the invention that utilize a blend of polyvinyl crosslinkers with non-vinyl and or dimodal crosslinkers, the effect on heat-treated capacity of all three types of crosslinkers is additive in nature. That is, if the amount of one crosslinker is increased the amount of another must be decreased to maintain the same overall heat-treated capacity. In addition, the proportion of the crosslinker components within the blend may be varied to achieve different resin properties and processing characteristics. In particular the polyvinyl crosslinkers of the invention are typically more expensive than non-vinyl or dimodal crosslinkers. Therefore the overall cost of the resin is reduced if a greater proportion of the crosslinker blend is composed of less expensive non-vinyl and or dimodal crosslinkers. However, the non-vinyl and dimodal crosslinkers of the invention function essentially as latent crosslinkers. That is, the crosslinking imparted to the resin by these agents is essentially not developed or seen until after the heat-treatment step. Little if any toughness is added to the hydrogel immediately after polymerization by use of such latent crosslinkers. This is an important concern for those processes for which a "tough" gel is desirable.

If too little of the total crosslinker blend is composed of polyvinyl crosslinker the polymerized hydrogel may not have sufficient toughness to be easily ground, processed, and dried. For this reason the proportion of polyvinyl crosslinker in the total crosslinker blend is preferably at least sufficient to produce a hydrogel that has enough toughness to be readily ground, processed, and dried. This toughness is inversely proportional to the centrifuged capacity of the resin after drying but before heat-treatment. The exact amount of polyvinyl crosslinker required in the blend to achieve this level of toughness will vary, but is enough to provide a centrifuged capacity of the resin after drying but before heat-treatment of preferably 45 g/g or less, more preferably 40 g/g or less, and most preferably 35 g/g or less.

Conventional additives which are well known in the art such as surfactants may be incorporated into the polymerization mixture which is polymerized. Polymerization can be accomplished under polymerization conditions in an aqueous or nonaqueous polymerization medium. Polymerization accomplished by processes which employ nonaqueous polymerization media may use various inert hydrophobic liquids which are not miscible with water, such as hydrocarbons and substituted hydrocarbons including halogenated hydrocarbons as well as liquid hydrocarbons having from 4 to 20 carbon atoms per molecule including aromatic and aliphatic hydrocarbons, as well as mixtures of any of the aforementioned media.

In one embodiment, the resin particles are prepared by contacting the reactive monomers and crosslinkers of the invention in an aqueous medium in the presence of a free radical or oxidation reduction (redox) catalyst system and a chlorine or bromine containing oxidizing agent under conditions such that a crosslinked hydrophilic resin is prepared. In another embodiment, the resin particles are prepared by contacting the reactive monomers and crosslinkers of the invention in an aqueous medium in the presence of a free radical or oxidation-reduction (redox) catalyst system under conditions such that a crosslinked hydrophilic resin is prepared. As used herein, aqueous medium means water, or water in admixture with a water-miscible solvent. Such water-miscible solvents include lower alcohols and alkylene glycols. Preferably the aqueous medium is water.

The monomers and crosslinkers are preferably dissolved, dispersed or suspended in a suitable polymerization medium, such as, for example, the aqueous medium at a concentration level of 15 percent by weight or greater, more preferably 25 percent or greater, and most preferably 29 percent or greater. The monomers and crosslinkers are preferably dissolved, dispersed or suspended in the aqueous medium.

Another component of the aqueous medium used to prepare the water-absorbent resin particles comprises a free radical initiator, which may be any conventional water soluble polymerization initiator including, for example, peroxygen compounds such as sodium, potassium and ammonium persulfates, caprylyl peroxide, benzoyl peroxide, hydrogen peroxide, cumene hydroperoxide, tertiary butyl diperphthalate, tertiary butyl perbenzoate, sodium peracetate and sodium percarbonate.

Conventional redox initiator systems can also be utilized, which are formed by combining the foregoing peroxygen compounds with reducing agents, such as, for example, sodium bisulfite, sodium thiosulphate, L- or iso-ascorbic acid or a salt thereof or ferrous salts. The initiator can comprise up to about 5 mole percent based on the total moles of polymerizable monomer present. More preferably the initiator comprises from 0.001 to 0.5 mole percent based on the total moles of polymerizable monomer in the aqueous medium.

An important aspect of a significant embodiment of the invention is the substantially uniform distribution within the resin particles of an oxidizing agent. Any suitable oxidizing agent which produces the desired particle properties may be used. Desirably, a chlorine or bromine containing oxidizing agent is used during the heating process. Preferred oxidizing agents are bromates and chlorates and chlorites. The counterion of the bromate or chlorate salt can be any counterion which does not significantly interfere in the preparation of the resin particles or their performance. Preferably, the counterions are alkaline earth metals ions or alkali metal ions. More preferred counterions are the alkali metals, with potassium and sodium even more preferred. The chlorine containing oxidizing agents are preferred. The oxidizing agent is present in sufficient amount such that after heat-treatment the residual monomer level is reduced and the desired balance of centrifuged absorption capacity and AUL is achieved.

If too much of the oxidizing agent is used, the ultimate properties of the resin particles are degraded. If an insufficient amount is added, the above described property improvements do not occur and the absorptive capacity will be low. Preferably, 10 ppm by weight or greater of a chlorine or bromine containing oxidizing agent based on the monomers is added, more preferably 50 ppm or greater and even more preferably 100 ppm or greater and most preferably 200 ppm or greater. Desirably, the amount of a chlorine or bromine containing oxidizing agent added is 2000 ppm or less by weight based on the monomers, more desirably 1000 ppm or less, preferably 800 ppm or less and most preferably 500 or less. The chlorine or bromine containing oxidizing agent may be added to the polymerization mixture or sprayed on the resulting hydrogel after polymerization. Preferably a chlorate or bromate salt is added. In the preferred embodiment of the invention, the chlorine or bromine containing oxidizing agent is added to the polymerization mixture.

The process of the invention may be performed in a batch manner wherein all of the reaction materials are contacted and the reaction proceeds, or it may take place with the continuous addition of one or more of the components during the reaction period. The polymerization mixture in the polymerization medium is subjected to polymerization conditions which are sufficient to produce the water-absorbent resin particles.

Preferably, the reaction is performed under an inert gas atmosphere, for example, under nitrogen or argon. The reaction may be performed at any temperature at which polymerization occurs, preferably 0° C. or greater, more preferably 25° C. or greater and most preferably 50° C. or greater.

The reaction mixture may be reacted for a time sufficient to result in the desired conversion of monomer to crossl inked hydrophilic resin. Preferably, the conversion is 95 percent or greater, more preferably 98 percent or greater.

Preferably, 25 mole percent or greater of the carboxylic acid units of the hydrophilic resin are neutralized with base, even more preferably 50 percent or greater and most preferably 65 percent or greater. This neutralization may be performed after completion of the polymerization. In a preferred embodiment the starting monomer mix has carboxylic acid moieties which are neutralized to the desired level prior to polymerization. The final polymer or the starting monomers may be neutralized by contacting them with a salt forming cation. Such salt-forming cations include alkaline metal, ammonium, substituted ammonium and amine based cations. Preferably, the polymer is neutralized with an alkali metal hydroxide such as, for example, sodium hydroxide or potassium hydroxide, or an alkali metal carbonate such as, for example, sodium carbonate or potassium carbonate.

It is also possible to prepare the resin of the current invention with the addition of recycled "fines" to the polymerization mixture. See PCT International Application with Publication No. WO 92/20723. "Fines" are generally considered to include, but are not limited to, the fraction of water-absorbent resin particle that passes through a 140 mesh screen when the dried and ground product is screened prior to heat-treatment. The amount of fines added to the polymerization mixture is, on a total solids basis, preferably less than 12 weight percent, more preferably less than 10 weight percent, and most preferably less than 8 weight percent.

It is also possible, however, to carry out the polymerization process using multiphase polymerization processing techniques such as inverse emulsion polymerization or inverse suspension polymerization procedures. In the inverse emulsion polymerization or inverse suspension polymerization procedures, the aqueous reaction mixture as herein before described is suspended in the form of tiny droplets in a matrix of a water-immiscible, inert organic solvent such as cyclohexane. Polymerization occurs in the aqueous phase, and suspensions or emulsions of this aqueous phase in an organic solvent permit better control of the exothermic heat of polymerization and further provide the flexibility of adding one or more of the aqueous reaction mixture components in a controlled manner to the organic phase.

Inverse suspension polymerization procedures are described in greater detail in Obayashi et al., U.S. Pat. No. 4,340,706; and in Flesher et. al. U.S. Pat. No. 4,506,052. When inverse suspension polymerization or inverse emulsion polymerization techniques are employed, additional ingredients such as surfactants, emulsifiers and polymerization stabilizers may be added to the overall polymerization mixture. When any process employing organic solvent is utilized, it is important that the hydrogel-forming polymer material recovered from such processes be treated to remove substantially all of the excess organic solvent. Preferably, the hydrogel-forming polymers contain no more than about 0.5 percent by weight of residual organic solvent.

During polymerization, the resin of the invention generally absorbs all of the aqueous reaction medium to form a hydrogel. The resin is removed from the reactor in the form of an aqueous hydrogel. Hydrogel as used herein refers to water swollen water-absorbent resin or resin particles. In preferred embodiments, such hydrogels comprise 15 to 50 percent by weight resin, with the remainder comprising water. In a more preferred embodiment the hydrogel comprises 25 to 45 percent resin. The hydrogel is preferably comminuted to granular form or particles, with particle sizes of 2 cm or less being more preferred. In multiphase polymerization, the water-absorbent resin hydrogel particles may be recovered from the reaction medium by azeotropic distillation and/or filtration followed by drying. If recovered by filtration then some means of removing the solvents present in the hydrogel must be used. Such means are commonly known in the art.

After removal from the reactor, the hydrogel resin may be optionally subjected to comminution, such as, for example, by a convenient mechanical means of particle size reduction, such as grinding. The size of the gel particles after particle size reduction should be such that homogeneous drying of the particles can occur. This particle size reduction can be performed by any means known in the art which gives the desired result. Preferably the particle size reduction is performed by chopping the hydrogel.

In the embodiment of the invention in which the oxidizing agent is added after polymerization, the ground hydrogel would next have applied to it a chlorine or bromine containing oxidizing agent dispersed or dissolved in a liquid so that the oxidizing agent is substantially uniformly distributed through the hydrogel particles. Preferably, the hydrogel is uniformly sprayed with an aqueous solution of the oxidizing agent of this invention. The concentration of the oxidizing agent solution is not critical, but should be dilute enough to provide an adequate volume of solution to ensure uniform distribution of the oxidizer within the hydrogel. Preferably, the concentration of the oxidizing agent solution is between 0.1 and 10 weight percent. Preferably, the oxidizing agent solution is applied to the hydrogel before any water moisture is removed. If the hydrogel is substantially dried prior to application of the oxidizing agent solution, the desired improvement in the absorption properties of the resin after heat-treatment is not seen.

Thereafter, the hydrogel resin particles are subjected to drying conditions to remove the polymerization medium and any dispersing liquid including the optional solvent and substantially all of the water.

The amount of residual water moisture in the polymer after drying will affect the properties of the resin after heat-treatment. That is because it has been found that the magnitude of the "chlorate effect" on greater post heat-treatment centrifuged absorption capacity and reduction in post heat-treatment residual monomer concentration depends on the moisture content of the resin after drying but before heat-treatment. Greater moisture levels lead to a greater "chlorate effect", and therefore greater post heat-treatment centrifuged absorption capacity (also referred to as heat-treated capacities) and lower post heat-treatment residual monomer concentration. If too little moisture is present the centrifuged absorption capacity of the resin will be low, and the residual monomer content will be high. If too much moisture is present the polymer will be difficult to process.

Desirably, the moisture content of the polymer after drying to remove the polymerization medium and any dispersing liquid including the optional solvent and substantially all of the water is between zero and 20 weight percent, preferably between 5 and 10 weight percent. The temperature at which the drying takes place is a temperature high enough such that the polymerization medium and liquid including water and optional solvent is removed in a reasonable time period, yet not so high so as to cause degradation of the resin particles, such as by breaking of the crosslink bonds in the resin. Preferably, the temperature of the resin particles during drying is 180° C. or less. Desirably, the temperature during drying is 100° C. or above, preferably, 120° C. or above and more preferably 150° C. or above.

The drying time should be sufficient to remove substantially all of the water and optional solvent. Preferably, a minimum time for drying is 10 minutes or greater, with 15 minutes or greater being preferred. Preferably, the drying time is 60 minutes or less, with 25 minutes or less being more preferred. In a preferred embodiment, drying is performed under conditions such that water, and optional solvent, volatilizing away from the absorbent resin particles is removed. This can be achieved by the use of vacuum techniques or by passing inert gases or air over or through the layers of resin particles. In a preferred embodiment, the drying occurs in dryers in which heated air is blown through or over layers of the resin particles. Preferred dryers are fluidized beds or belt dryers. Alternatively a drum dryer may be used. Alternatively the water may be removed by azeotropic distillation. Such techniques are well known in the art.

During drying the water-absorbent resin particles may form agglomerates and may then be subjected to comminution, such as, for example, by mechanical means for breaking up the agglomerates. In a preferred embodiment, the water-absorbent resin particles are then subjected to mechanical particle reduction means. Such means can include chopping, cutting and/or grinding. The object is to reduce the particle size of the resin particles to a particle size acceptable in the ultimate end use. In a preferred embodiment, the resin particles are chopped and then ground. The final particle size is preferably 2 mm or less, more preferably 0.8 mm or less. Preferably the particles have a size of 0.01 mm or greater, more preferably 0.05 mm or greater.

In a preferred embodiment after drying and particle size reduction, the resin particles are subjected to a heat-treatment step. Suitable devices for heat-treatment include, but are not limited to, rotating disc dryers, fluid bed dryers, infrared dryers, agitated trough dryers, paddle dryers, vortex dryers, and disc dryers. One of ordinary skill in the art would vary the time and temperature of heat-treatment as appropriate for the heat transfer properties of the particular equipment used, and for the particular.

The time period and temperature of the heat-treatment step are chosen such that the absorption properties of the resin are improved as desired. The resin particles are desirably heated at a temperature of 170° C. or above, more desirably 190° C. or above, preferably at 200° C. or above and most preferably at 210° C. or above. Below 170° C. no improvement in the absorption properties is seen. The temperature should not be so high as to cause the resin particles to degrade. Preferably, the temperature is 250° C. or below and more preferably 235° C. or below.

The resin particles are heated to the desired heat-treatment temperature and preferably maintained at such temperature for 1 minute or more and more preferably 5 minutes or more and most preferably 10 minutes or more. Below 1 minute no improvement in properties is generally seen. If the heating time is too long it becomes uneconomical and there is a risk that the resin particles maybe damaged. Preferably resin particles are maintained at the desired temperature for 60 minutes or less, preferably 40 minutes or less. Above 60 minutes no significant improvement in properties is noticed. The properties of the resin particles can be adjusted and tailored by adjustment of the temperature and the time of the heating step. Longer heat times generally result in higher absorption under load, lower level of extractables and a lower absorption capacity. The use of higher temperatures for the heating step generally result in higher absorption under load, and lower level of extractables.

After heat-treatment the resin particles may be difficult to handle due to the static electricity. It may be desirable to rehumidify the particles to reduce or eliminate the effect of the static electricity. Methods of humidification of dry resins are well known in the art. In a preferred mode, the dry particles are contacted with water vapor. The dry particles are contacted with a sufficient amount of water to reduce or eliminate the effects of the static electricity, yet not so much so as to cause the particles to agglomerate. Preferably the dry particles are humidified with 0.3 percent or more by weight of water and more preferably 5 percent or more by weight of water, preferably, the dry particles are humidified with 10 percent or less by weight of water and more preferably 6 percent or less by weight of water. Optionally, agglomeration prevention or rehydration additives may be added to the crosslinked hydrophilic resin. Such additives are well known in the art and include surfactants and inert inorganic particles such as silica; see, for example, U.S. Pat. Nos. 4,286,082; 4,734,478; and DE 2706135.

The resin particles of this invention have a better balance of properties than previously known water-absorbent resins. The measured values for absorption under load are found to be consistently high at increasingly higher loads, such as, for example, 2.1 kPa ( 0.3 psi), 4.1 kPa (0.6 psi), 5.5 kPa (0.8 psi) and 6.9 kPa (1.0 psi). This is illustrated by FIG. 1, which compares the absorption under load of resin particles currently available on the market with Example 21 of the current invention. FIG. 1 is the plot of absorption under load versus pressure after 60 minutes absorption for DRYTECH™ 2000 water-absorbent resin (trademark of The Dow Chemical Company), Hoechst Celanese SANWIT IM™ 3400 water-absorbent resin, Stockhausen FAVOR SXM™ 100 water-absorbent resin, and Example 21 of the current invention. The values for zero load of the plot are actually the measured centrifuged capacity values after 30 minutes absorption. As can be seen from the plot the resin of the current invention exhibits consistently higher AUL at increasingly higher loads as compared to commercially available water-absorbent resins.

The water-absorbent resin particles of the invention preferably exhibit a residual monomer level of 800 ppm by weight or less based on particle weight, more preferably ppm or less, even more preferably 500 ppm or less and most preferably 300 ppm or less.

It is desirable that the water-absorbent resin particles exhibit a centrifuged absorption capacity (capacity) of 25 g/g or greater, preferably 28 g/g or greater and more preferably 30 g/g or greater. In a highly preferred embodiment, the centrifuged absorption capacity is 37 g/g or greater.

Desirably the absorption under load of the water-absorbent resin particles at 0.3 psi is 26 or greater, more preferably 28 g/g or greater and even more preferable 31 g/g or greater. Preferably, the absorption under load at 0.6 psi is 16 g/g or greater and more preferably 20 g/g or greater. Preferably, the absorption under load at 1.0 psi is 9 g/g or greater and more preferably 15 g/g or greater.

It is desirable that the water-absorbent resin particles exhibit a centrifuged absorption capacity of 26 g/g or greater and an absorption under load of 24 g/g or greater at 0.6 psi load. While the aforementioned values are desirable, preferred embodiments are those wherein (i) the resin particle has an absorption under load of 17 g/g or greater at 0.8 psi load, or (ii) the resin particle has an absorption under load of 14 g/g or greater at 1 psi load, or (iii) the resin particle has an absorption under load of 22 g/g or greater at 0.8 psi load and the resin particle has an absorption under load of 20 g/g or greater at 1 psi load, or (iv) the resin particle has a centrifuged absorption capacity of 30 g/g or greater, or (v) the resin particle has a centrifuged absorption capacity of 30 g/g or greater and an absorption under load of 17 g/g or greater at 0.8 psi load, or (vi) the resin particle has a centrifuged absorption capacity of 30 g/g or greater and an absorption under load of 14 g/g or greater at 1 psi load, or (vii) the resin particle has a centrifuged absorption capacity of 30 g/g or greater and an absorption under load of 22 g/g or greater at 0.8 psi load, or (viii) the resin particle has a centrifuged absorption capacity of 37 g/g or greater and an absorption under load of 17 g/g or greater at 0.8 psi load.

The water-absorbent resin particles of this invention can be used in any use wherein absorption and binding of aqueous fluids is desired. In a preferred embodiment, the water-absorbent resin particles of this invention are mixed into or attached to a structure of absorbent material such as synthetic or natural fibers or paper based woven or nonwoven fibers to form a structure. In such a structure the woven or nonwoven structure functions as a mechanism for wicking and transporting via capillary action the fluid to the water-absorbent resin particles which bind and retain such fluids. Examples of such structures are diapers, adult incontinence structures, and sanitary napkins.

The absorbent structures according to the present invention comprise means to contain the water-absorbent resin particles. Any means capable of containing the described water-absorbent resin particles, which means is further capable of being positioned in a device such as an absorbent garment, is suitable for use in the present invention. Many such containment means are known to those skilled in the art. For example, the containment means may comprise a fibrous matrix such as an airlaid or wetlaid web of cellulosic fibers, a meltblown web of synthetic polymeric fibers, a spunbonded web of synthetic polymeric fibers, a coformed matrix comprising cellulosic fibers and fibers formed from a synthetic polymeric material, airlaid heat-fused webs of synthetic polymeric material or open-celled foams. In one embodiment, it is preferred that the fibrous matrix comprise less than 10 preferably less than 5 weight percent of cellulosic fibers.

Alternatively, the containment means may comprise two layers of material which are joined together to form a compartment, which compartment contains the water-absorbent resin particles. In such a case, at least one of the layers of material should be water-pervious. The second layer of material may be water-pervious or water-impervious. The layers of material may be cloth-like wovens or nonwovens, closed or open celled foams, perforated films, or may be fibrous webs of material. When the containment means comprises layers of material, the material should have a pore structure small enough or tortuous enough to contain the majority of the water-absorbent resin particles.

Further, the containment means may comprise a support structure, such as a polymeric film, on which the water-absorbent resin particles is affixed. The water-absorbent resin particles may be affixed to one or both sides of the support structure which may be water-pervious or water-impervious.

In one very desirable embodiment of the present invention, it has been found that when the containment means comprises a meltblown web of synthetic polymeric fibers, it is desirable that the meltblown fibers be hydrophilic. Synthetic polymeric fibers are considered to be hydrophilic when the fibers have a contact angle of water in air of less than 90 degrees. For the purposes of this application, contact angle measurements are determined as set forth by Good and Stromberg in "Surface and Colloid Science", Vol. II (Plenum Press, 1979). The fibers may be rendered hydrophilic by using a hydrophilic polymeric material to form such fibers or, by treating generally hydrophobic fibers with a surface treatment, which renders the fibers hydrophilic.

Specifically, hydrophilic fibers can be formed from an intrinsically hydrophilic polymer such as a block copolymer of nylon, for example, nylon-6, and a polyethylene oxide diamine. Such block copolymers are commercially available from Allied-Signal Inc. under the trade designation Hydrofil™. The hydrophilic fiber may also be formed from a water-swellable, substantially water-insoluble superabsorbent polymeric material such as a thermoplastic material described in U.S. Pat. No. 4,767,825 issued Aug. 30, 1988, to Pazos, et al. Alternatively, the meltblown fibers may be formed from an intrinsically hydrophobic polymer such as a polyolefin or polyester which has been surface modified to provide a generally nonfugitive hydrophilic surface. Such a surface modified polyethylene is commercially available from The Dow Chemical Company under the trade designation Aspun™ wettable polyethylene.

When the hydrophilic fibers are formed by applying a hydrophilic surface treatment to a generally hydrophobic polymer, it is believed desirable to employ a generally non-fugitive surface treatment in order to obtain the desired performance standards. Absorbent structures employed in absorbent garments such as diapers are often subjected to multiple insults of urine, if the surface treatment is fugitive it may be washed off with the initial insult thus, exposing the hydrophobic fiber surface. The hydrophobic fiber surface may impede the absorption performance of the absorbent structure. Of course, there are instances where hydrophobic fibers may be employed, particularly at lower concentrations of fiber and higher concentrations of water-absorbent resin particles.

In another preferred embodiment, wherein the containment means comprises two layers of material which layers are joined to form a compartment adapted to contain the water-absorbent resin particles, the two layers are suitably formed from any material capable of containing the water-absorbent resin particles including woven and non-woven material such as, for example, airlaid or wetlaid fibers, meltblown fibers, spunbonded fibers or colormeal fibers, and are joined to form a compartment by heat fusion, sonic bonding or adhesives. Clearly, a wide variety of materials may be employed to form the two layers and to join the layers together to form the compartment.

As indicated above, because the superabsorbent resin particle has the described combination of absorption characteristics including centrifuged absorption capacity and absorption under load, and does not need to be maintained in a fibrous matrix at relatively low degrees of concentration in order to avoid gel blocking, the described water-absorbent resin particles can be present in the absorbent structures in relatively high concentrations compared to known absorbent structures. Specifically, the absorbent structures according to the present invention suitably comprise from 50 to 100 weight percent of water-absorbent resin particles based on total weight of the containment means and the water-absorbent resin particles. Preferably, the absorbent structures comprise from 70 to 100 weight percent of water-absorbent resin particles based on total weight of the containment means and the water-absorbent resin particles. Most preferably, the absorbent structures comprises from 75 to 99 weight percent of water-absorbent resin particles based on total weight of the containment means and the water-absorbent resin particles.

Because the water-absorbent resin particles present in the absorbent structures of the present invention can be present in high concentrations, the absorbent structures of the present invention can be relatively thin and have a relatively small volume and still function in a desirable manner. Suitably, the absorbent structures according to the present invention have an average thickness of less than 0.2 inches (5.1 millimeters), preferably less than 0.15 inches (3.8 millimeters). Moreover, the absorbent structures suitably define a major planar surface having a surface area less than 75 square inches (484 square centimeters), preferably less than 50 square inches (323 square centimeters) and most preferably less than 40 square inches (258 square centimeters).

As used herein, reference to the average thickness of an absorbent structure is intended to refer to the average of a number of thickness measurements taken under an a ed load of about 1.3 kPa (0.2 psi). The number of thickness measurements taken is sufficient to represent the average thickness of the entire absorbent structure.

The absorbent structures of the present invention are desirably relatively flexible to enhance comfort during use. For the purposes of this invention, such absorbent structures will be considered to possess the desired degree of flexibility when they have a Gurley stiffness value of less than 2 grams, preferably less than 1 gram.

The absorbent structures according to the present invention are suited to absorb many fluids including body fluids such as, for example, urine, menses, and blood and are suited for use in absorbent garments such as diapers, adult incontinent products and bed pads; in catamenial devices such as sanitary napkins and tampons; and in other absorbent products such as, for example, wipes, bibs and wound dressings. Accordingly, in another aspect, the present invention relates to an absorbent garment comprising an absorbent structure as described above.

Use of the described absorbent structures in absorbent garments, allows for the formation of an absorbent garment which is able to rapidly receive a discharged liquid and yet which garment is thin. The average thickness of an absorbent garment according to this aspect of the invention is defined as the average thickness of the garment in the area of the garment which is coextensive with the absorbent structure contained thereon. The average thickness is determined as set forth above in connection with determining the average thickness of the absorbent structure, except that the absorbent garment is employed rather than just the absorbent structure.

Absorbent garments according to this aspect of the present invention suitably have an average thickness of less than 0.25 inch (6.4 millimeters) preferably, less than 0.22 inch (5.6 millimeters), and most preferably less than 0.20 inch (5.1 millimeters).

The following examples are included to illustrate the invention, and do not limit the scope of the claims. Unless otherwise stated all parts and percentages are by weight based on the polymerizable components of the polymerization mixture.

Resin Preparation Procedure 1

Samples were prepared in a reactor with a 2-L glass resin kettle bottom, a stainless steel agitator assembly, and a high-torque stirring motor with gear reducers. The kettle bottom has a glass jacket to allow for heating or cooling of the contents using a separate water-circulating temperature bath. The reactor can be sealed with an O-ring that fits into grooves in the kettle bottom and the steel agitator top.

The monomer mix was prepared by adding 319.31 g of acrylic acid to a beaker, followed by water (406.29 g) Versenex® 80 (trademark of The Dow Chemical Company) chelating agent (1.00 g), vinyl crosslinker, and optionally non-vinyl or dimodal crosslinker. To this mixture was added, with stirring, a solution of 152.78 g of sodium carbonate in 381.95 g of water. In those reactions that included the oxidizing agent of this invention the required amount of a 5 percent solution was added next. The monomer mix was loaded to the reactor under vacuum via a loading tube and the mixture was sparged with nitrogen for 1 hour to remove dissolved oxygen. For those reactions utilizing allyl methacrylate or volatile non-vinyl or dimodal crosslinker, it was added to the reactor after sparging and five minutes before the initiators. Next in sequence, a 30 percent hydrogen peroxide in water solution (0.64 mL), 10 percent sodium persulfate in water (5.12 mL) and 10 percent sodium erythorbate in water (0.6 mL) were added via syringe. The exothermic reaction typically reached a peak temperature of about 85° C. after about 30 minutes at which point the vessel was heated to 65° C. for 3 hours.

The resulting product was dried on a nylon mesh screen for 16 hours at 100° C. in a forced air oven, then was ground in a food blender and screened to a 20 to 100 mesh cut.

Resin Preparation Procedure 2

Samples were prepared in a 200 L polymerization reactor with a stainless steel agitator assembly and a high torque stirring motor with gear reducers. This assembly allowed grinding of the gel formed during polymerization. The reactor jacket was hollow and allowed heating or cooling of the reactor content by using a separate water circulating temperature device. The reactor was sealed and connected to a vacuum system, by which it was possible to cool the gel mass by pulling a vacuum.

37.2 kg acrylic acid was added slowly in a separate vessel to a mixture of 40.1 kg of an aqueous NaOH solution (50 weight percent) and 77 kg process water in such a way to prevent the temperature from going above 38° C. 70 g of a solution of triethylene diamine pentaacetate in water (Versenex® 80 trademark of The Dow Chemical Company) and 13 g partially hydrolyzed polyvinyl alcohol, dissolved in 130 mL pure water, were added to the premix. The appropriate level of crosslinker was added to 15.9 kg of pure acrylic acid and the mixture obtained was poured into the premix after the premix was cooled to room temperature again. The monomer mixture obtained was pumped into the reactor, while purging the liquid with nitrogen. 900 g of an aqueous sodium peroxodisulfate solution (10 weight percent) and 68 g hydrogen peroxide (30 weight percent active) were added with a syringe to the reactor. A vacuum was pulled twice in order to remove oxygen and the reactor's headspace was filled with nitrogen again. The reaction was initiated by the addition of 8 g ascorbic acid dispersed in 80 mL water. With the beginning of the polymerization, the external heater was set to 70° C., and a slow nitrogen flow was maintained through the reactor. The contents were cooled to 70° C. after the polymerization medium reached its peak temperature (at approximately 80° C.) by pulling a vacuum. The gel was kept for 1 hour at 70° C. in the reactor, minced after off loading and dried in a belt drier for 20 minutes with an air stream at 170° C.

A part of the resulting dry product was ground in a lab mill, then screened to a 30 to 50 mesh cut.

Resin Preparation Procedure 3

138.2 g of a 20 percent aqueous solution of sodium hydroxide and 35.2 g of deionized water were loaded into a glass flask which had a hollow jacket connected to a cooling water source. 51.6 g of acrylic acid were added slowly and the mixture was cooled to room temperature. Then 0.1 g of a 40 percent active solution of diethylene triamine pentaacetate in water (Versenex® 80) and 0.4 g of polyvinyl alcohol solution (5 weight percent in water) were added to the mixture. The appropriate amount of the crosslinker was dissolved in 1.9 g acrylic acid and the resulting mixture was added to the flask. The monomer mixture prepared was placed in a 250 mL round bottom flask equipped with a plane flange at the top. The flange was sealed with a lid which contained four openings, of which two were reserved for the thermometer and the $N_2$ supply, one opening was connected to the vent system and the fourth one was sealed with a septum. The monomer mixture was purged for at least 10 minutes with a rapid nitrogen stream to remove traces of oxygen. The nitrogen bubbling was reduced and 1.7 g of a 1.5 percent aqueous hydrogen peroxide solution, 1.24 g of a 10 weight percent aqueous sodium persulfate solution and 1.1 g of a 1 percent aqueous ascorbic acid solution were introduced in sequence to the reaction mixture using a syringe through the septum. Polymerization started about 5 minutes after introduction of ascorbic acid at a temperature of 24° C.

After the peak temperature of 70° C. was reached the flask was placed in a water bath for 60 minutes at 70° C. Then the reactor was opened and a mass of aqueous polymer gel was collected. The aqueous polymer gel was cut into small pieces and dried overnight in an oven at 105° C. The product was ground and screened to a 30 to 50 mesh cut. The particle size fraction between 0.595 and 0.297 mm (30 to 50 mesh) was used for performance and quality analysis. For gel strength measurement the fraction 0.177 mm to 0.297 mm (50–80 mesh) was used. The 30 to 50 mesh fraction was collected and analyzed for 30 minutes centrifuge absorption capacity (CC), g/g absorption under load (AUL), g/g and 16 hour extractables fraction (percent Ext).

Resin Preparation Procedure 4

Polymer was prepared in a 30 gallon (120 L) gel reactor. The monomer solution was first prepared in a 50 gallon mix tank. Acrylic acid 22 kg (48 pounds), Versenex® 80 (29 g), poly(vinyl alcohol) (5 percent, 109 g), HE-TMPTA (SARTOMER® 9035, 185.2 g), and 23 kg (50 pounds) of water were first loaded to the mix tank, followed by the sodium carbonate (as a 22 weight percent solution, 10 kg (23 pounds). During and after the neutralization an air purge was applied to the bottom of the mix tank to keep the acrylic acid inhibitor active. After the carbon dioxide evolution was complete, the potassium chlorate solution (if added, 5.5 g solids) was added. Any recycled fines to be used 2 kg (4.4 pounds) at 7 percent level were then loaded to the mix tank and mixed for 10 minutes before transferring to the gel reactor. The hydrogen peroxide (50.8 g) and sodium persulfate (36.0 g) were added to the reactor, and then the mixture was deoxygenated for 30 minutes with nitrogen at 20 L/minutes. The sodium erythorbate (3.5 g) was then added.

The reaction exothermed adiabatically until vacuum was initiated at 80° C. The peak temperature was 84° C. The polymer was then held at 65° C. for 3 hours before cooling. The polymerized gel was removed from the reactor and ground in a meat grinder with 0.375 inch holes to break up large lumps. Gel was dried in a tray drier on perforated trays at 17 kg/m$^2$ (3.6 pounds/ft$^2$) for a total of 35 minutes. The samples were then ground in a food blender and screened to a 20 to 100 mesh cut.

Heat-Treatment Procedure 1

For heat-treatment 100 g of resin was spread evenly onto a 20×30 cm (8×12 inch) aluminum tray and placed in a 220° C. forced air oven for 40 min.

Heat-Treatment Procedure 2

The heating was performed by preheating a zone with a hot air gun. Once the target temperature was reached and stabilized, the sample was placed in the zone and a contact thermometer was placed in contact with the sample. The temperature of the sample was monitored until it stabilized at the target temperature. The sample was maintained at the target temperature for the desired time.

Heat-Treatment Procedure 3

For heat-treatment, 100 g of resin was spread evenly onto a 20×30 cm (8×12 inch) aluminum tray and placed in a 230° C. forced-air oven for 40 minutes.

Performance and quality of water-absorbent resin particles prepared were measured by the following methods.

Centrifuged Absorption Capacity 200 mg of water-absorbent resin particles was placed within a sealable tea bag (63.5 by 76.2 mm), immersed for 30 minutes into a 0.9 weight percent saline (sodium chloride) solution and then centrifuged for three minutes at 1600 rpm. The weight ratio of saline solution absorbed to water-absorbent resin particles was determined and reported as the centrifuged absorption capacity (CC).

Absorption Under Load

A nylon screen (50 by 50 mm; 100 mesh) was put on top of a perforated metal plate (holes with 5 mm) followed by a filter paper and finally by a stainless steel cylinder of 26 mm inner diameter, 37 mm outer diameter and a height of 50 mm, whose both ends were open. 167 mg of water-absorbent resin particles was placed into the cylinder and evenly distributed, covered by a nonwoven sheet of a diameter of 26 mm and finally pressed down with a plastic piston of 26 mm diameter which carries the weight. The total weight of piston and cylinder is 109.4 g to give a 2.1 kPa (0.3 psi) load. Proportionately heavier pistons were used to apply loads of 4.1, 5.5, 6.2 and 6.9 kPa (0.6, 0.8, 0.9 and 1.0 psi),. The metal plate with the product in the cylinder on top was immersed into the 0.9 percent saline solution such that the nylon screen and the water surface had the same level so that the filter paper and the water-absorbent resin particles are able to absorb water without any hydrostatic pressure. A soak time of one hour was applied. The plate was removed from the water reservoir and the excess water in the holes of the plate and in the nylon screen was soaked up by paper tissues. Then the weight was removed from the swollen gel and the gel was weighed. The weight ratio of saline solution absorbed under load to water-absorbent resin particles thus determined was reported as the absorption under load (AUL).

Extractables

I g of water-absorbent resin particles and 185 mL of 0.9 percent saline solution were placed in a 250 mL jar which was capped and put on a shaker for 16 hours. A part of the extraction solution was filtered. With the aid of a Metrohm Titroprocessor, the pH of a defined volume of the filtrate was adjusted to pH 10 by 0.1 N NaOH and finally titrated to pH 2.7 by 0.1 N hydrochloric acid, to determine the amount of extractable materials which was in the filtrate.

Residual Monomer

Residual acrylic acid was determined by adding 1 g of polymer to 185 g (200 g for Examples 49–72) of 0.9 percent sodium chloride solution and shaking the mixture for 16 hours. A sample of the filtrate was injected into a liquid chromatograph utilizing a ODS column and UV detection at about 205 nm. The residual monomer was calculated by comparing the peak area of the acrylic acid peak to that of a standard sample.

Percent Moisture

The percent moisture values reported herein are defined as the percent weight loss of a 10 g sample of ground resin in a circulating air oven at 105° C. over 3 hours. Additional weight loss during pre-treatment was measured by difference.

In the examples that follow, concentrations are measured in ppm based on the monomer acrylic acid. The terms "Before" or "Before Heat-Treatment" refer to the properties of the polymer after drying and sizing but before any heat-treatment. The terms "After" or "After Heat-Treatment" refer to the properties of the polymer after heat-treatment. Entries of "ND" mean the value was not determined.

EXAMPLES 1–8

Use of Polyethylene Glycol Based

Crosslinkers—Table 1

These examples illustrate the use of the present invention with crosslinkers based on polyethylene glycol: DEGDA (diethylene glycol diacrylate), TEGDA (tetraethylene glycol 200 diacrylate), PEG DA (polyethylene glycol 400 diacrylate), and PEGDMA (polyethylene glycol 600 dimethacrylate). Examples 2, 4, 6, and 8 show the present invention, in which 300 ppm of potassium chlorate was added to the reaction mixture prior to polymerization. Examples 1, 3, 5, and 7 show the result obtained when the oxidizing agent of this invention is omitted. (Resin Preparation Procedure 1. Heat-Treatment Procedure 1.)

TABLE 1

Use of Polyethylene Glycol Based Crosslinkers

| Ex. No. | Cross-linker | g | $ClO_3$ present | 0.3 psi AUL (g/g) Before Heat-Treatment / After Heat-Treatment | 0.6 psi AUL (g/g) Before / After | CC (g/g) Before / After | Ext (%) Before / After | Res AA (ppm) Before / After |
|---|---|---|---|---|---|---|---|---|
| 1 | DEGDA | 0.47 | No | 8.3 / 24.5 | 8.3 / 22.0 | 40.1 / 23.2 | 6.7 / 2.3 | 338 / 1294 |
| 2 | DEGDA | 0.47 | Yes | 8.7 / 32.1 | 8.3 / 23.0 | 37.4 / 33.6 | 7.0 / 3.9 | 271 / 712 |
| 3 | TEGDA | 0.60 | No | 15.4 / 28.5 | 8.9 / 22.5 | 35.4 / 25.4 | 5.6 / 3.3 | 269 / 738 |
| 4 | TEGDA | 0.60 | Yes | 15.4 / 31.5 | 8.9 / 19.9 | 35.3 / 36.8 | 5.7 / 4.0 | 505 / 851 |
| 5 | PEGDA | 1.02 | No | 23.1 / 26.6 | 9.9 / 22.8 | 32.1 / 26.4 | 4.1 / 2.7 | 263 / 706 |
| 6 | PEGDA | 1.02 | Yes | 25.7 / 32.5 | 11.9 / 22.2 | 32.7 / 36.1 | 3.8 / 3.5 | 337 / 782 |
| 7 | PEGDMA | 1.63 | No | 9.2 / 22.3 | 7.9 / 20.3 | 37.3 / 21.0 | 10.9 / 2.9 | 465 / 1866 |
| 8 | PEGDMA | 1.63 | Yes | 10.3 / 28.0 | 8.3 / 21.6 | 34.4 / 32.7 | 10.7 / 9.7 | 540 / 989 |

From these examples, it is clear that with these crosslinkers the combination of an oxidizing agent and the heat-treatment (chlorate effect) of this invention results in product that has a higher combination of CC and high load AUL then possible with neither or just one of these factors.

EXAMPLES 9–16

Use of TMPTA Based

Crosslinkers—Table 2

These examples illustrate the use of the present invention with crosslinkers based on trimethylolpropane triacrylate TMPTA. HE15 is SARTOMER® 9035, the triacrylate of the polyol obtained from reaction of one mole of trimethylolpropane with about 15 moles of ethylene oxide. HE3 is SARTOMER® 454, the triacrylate of the polyol obtained from reaction of one mole of trimethylolpropane with about 3 moles of ethylene oxide. HE20 is SARTOMER® 415, the triacrylate of the polyol obtained from reaction of one mole of trimethylolpropane with about 20 moles of ethylene oxide. Examples 10 and 12–16 show the present invention, in which 300 ppm of potassium chlorate was added to the reaction mixture prior to polymerization. Examples 9 and 11 show the result obtained when the oxidizer of the present invention is omitted. (Resin Preparation Procedure 1. Heat-Treatment Procedure 1.)

(hexane diol diacrylate). Examples 18 and 20 show the present invention, in which 300 ppm of potassium chlorate was added to the reaction mixture prior to polymerization. Examples 17 and 19 show the result obtained when the oxidizer of the present invention is omitted. (Resin Preparation Procedure 1. Heat-Treatment Procedure 1.)

TABLE 2

Use of TMPTA Based Crosslinkers

Properties: Before Heat-Treatment / After Heat-Treatment

| Ex. No. | Cross-linker | g | ClO$_3$ present | 0.3 psi AUL (g/g) | 0.6 psi AUL (g/g) | CC (g/g) | Ext (%) | Res AA (ppm) |
|---|---|---|---|---|---|---|---|---|
| 9 | TMPTA | 0.40 | No | 16.7 | 9.0 | 34.0 | 6.0 | 345 |
|   |       |      |    | 24.1 | 19.0 | 26.1 | 3.6 | 1257 |
| 10 | TMPTA | 0.40 | Yes | 23.6 | 9.6 | 31.5 | 6.1 | 355 |
|    |       |      |     | 28.2 | 15.5 | 34.6 | 11.0 | 691 |
| 11 | HE15 | 1.28 | No | 18.6 | 9.2 | 33.1 | 3.7 | 426 |
|    |      |      |    | 25.2 | 22.5 | 24.1 | 2.3 | 1136 |
| 12 | HE15 | 1.28 | Yes | 26.2 | 11.4 | 31.5 | 3.0 | 410 |
|    |      |      |     | 30.9 | 23.9 | 33.3 | 7.5 | 576 |
| 13 | HE15 | 0.96 | Yes | 22.4 | 9.7 | 33.1 | 3.8 | 941 |
|    |      |      |     | 31.2 | 20.2 | 37.4 | 12.2 | 571 |
| 14 | HE15 | 1.92 | Yes | 27.7 | 15.4 | 28.2 | 2.0 | 340 |
|    |      |      |     | 29.9 | 25.1 | 29.1 | 4.0 | 712 |
| 15 | HE3 | 0.57 | Yes | 13.5 | 8.5 | 34.9 | 5.2 | 314 |
|    |     |      |     | 26.8 | 18.8 | 28.1 | 10.5 | 267 |
| 16 | HE20 | 1.57 | Yes | 25.3 | 10.1 | 30.6 | 3.8 | 254 |
|    |      |      |     | 28.9 | 21.7 | 29.0 | 6.0 | 278 |

These examples show that the chlorate effect of the present invention is effective with a wide range of trimethylolpropane triacrylates at producing resin with both high CC and high AUL.

TABLE 3

Use of Propoxyl or Hydrocarbon Based Crosslinkers

Properties: Before Heat-Treatment / After heat-treatment

| Ex. No. | Cross-linker | g | ClO$_3$ present | 0.3 psi AUL (g/g) | 0.6 psi AUL (g/g) | CC (g/g) | Ext (%) | Res AA (ppm) |
|---|---|---|---|---|---|---|---|---|
| 17 | TPGDA | 0.66 | No | 10.2 | 8.4 | 38.2 | 5.4 | 224 |
|    |       |      |    | 26.0 | 21.2 | 27.6 | 3.1 | 370 |
| 18 | TPGDA | 0.66 | Yes | 13.1 | 9.1 | 35.5 | 5.1 | 343 |
|    |       |      |     | 30.9 | 16.7 | 37.9 | 12.6 | 134 |
| 19 | HODA | 0.50 | No | 13.7 | 9.0 | 36.4 | 5.3 | 286 |
|    |      |      |    | 23.4 | 20.9 | 22.2 | 3.2 | 1184 |
| 20 | HODA | 0.50 | Yes | 15.5 | 9.1 | 35.1 | 5.0 | 333 |
|    |      |      |     | 29.0 | 24.2 | 29.2 | 3.3 | 745 |

EXAMPLES 17–20

Use of Propoxyl or Hydrocarbon Based Crosslinkers—Table 3

These examples show the use of the present invention with TPGDA (tripropylene glycol diacrylate) and HODA These examples show that the chlorate effect of the present invention works with crosslinkers that are propoxylated or largely hydrocarbon in nature.

EXAMPLES 21-26

Influence of Crosslinker Concentration—Table 4

The crosslinker used was HE-TMPTA (SARTOMER® 9035), the triacrylate of the polyol obtained from reaction of one mole of trimethylolpropane with about 15 moles of ethylene oxide, also available from Cray Valley under the trademark and designation CRAYNOR™ 435. Added to each initial monomer mix was 305 ppm of potassium chlorate. The particles were heated at 230° C. for 15 minutes except for Example 26 which was heated for 20 minutes at 230° C. (Resin Preparation Procedure 2. Heat-Treatment Procedure 2.)

TABLE 4

Influence of Crosslinker Concentration

| | | Properties | Before Heat-Treatment | | |
| | | | After Heat-Treatment | | |

| Ex. No. | Amount (ppm) | 0.3 psi AUL (g/g) | 0.6 psi AUL (g/g) | CC (g/g) | Ext (%) | Res AA (ppm) |
|---|---|---|---|---|---|---|
| 21 | 8000 | 21.6 | ND | 31.5 | 6.8 | 463 |
|    |      | 31.6 | 26.4 | 31.7 | 6.9 | 444 |
| 22 | 5000 | 14.5 | ND | 35.7 | 11.8 | 308 |
|    |      | 31.5 | 26.3 | 34.0 | 11.9 | 263 |
| 23 | 4000 | 10.3 | ND | 38.0 | 12.5 | 311 |
|    |      | 32.8 | 25.7 | 38.6 | 10.8 | 243 |
| 24 | 3000 | 9.7 | ND | 40.9 | 14.7 | 335 |
|    |      | 34.4 | 21.8 | 44.3 | 17.2 | 315 |
| 25 | 1550 | 9.2 | ND | 48.2 | 23.1 | 259 |
|    |      | 32.7 | ND | 48.4 | 36.5 | 268 |
| 26 | 3050 | 6.3 | ND | 45.5 | 18.4 | 174 |
|    |      | 31.3 | 18.4 | 34.9 | 10.7 | 550 |

EXAMPLES 27-30

Use of Allyl Methacrylate as Crosslinker—Table 5

These examples demonstrate the use of allyl methacrylate (AMA) as a crosslinker at 3500 ppm concentration. Examples 28-30 show the present invention, in which 305 ppm of potassium chlorate was added to the polymerization mixture prior to polymerization. Example shows the result obtained when the oxidizing agent is omitted. The heating temperature (HT Temp) is varied and the residence time after reaching the target temperature is 40 minutes. (Resin Preparation Procedure 2. Heat-Treatment Procedure 2.)

TABLE 5

Use of Allyl Methacrylate as Crosslinker

| | | Before Heat-Treatment | | | |
| | | After Heat-Treatment | | | |

| Ex. No. | HT Temp (°C.) | 0.3 psi AUL (g/g) | CC (g/g) | Ext (%) | Res AA (ppm) |
|---|---|---|---|---|---|
| 27 | 210 | 25.6 | 26.5 | 5.2 | 678 |
|    |     | 26.6 | 26.4 | 5.0 | 895 |
| 28 | 200 | 24.7 | 26.3 | 5.6 | 580 |
| 29 | 210 | 29.6 | 35.0 | 10.9 | 818 |
|    |     | 24.7 | 26.3 | 5.6 | 580 |
| 30 | 220 | 28.8 | 37.9 | 13.7 | 866 |
|    |     | 24.7 | 26.3 | 5.6 | 580 |
|    |     | 29.4 | 40.9 | 18.9 | 905 |

Optimum heating temperatures for allyl methacrylate crosslinked product are between 200° C. and 220° C. The allyl methacrylate crosslinked product showed an increase in centrifuge capacity with heat-treatment even without the oxidizer of the current invention but addition of potassium chlorate enhances this effect. Lower heating temperatures are preferred for allyl methacrylate crosslinked products in order to achieve good absorption values and a low percentage of extractable materials.

EXAMPLES 31-43

Use of Non-Vinyl Crosslinkers With HE-TMPTA—Table 6

These examples used a blend of HE-TMPTA (SARTOMER® 9035) vinyl crosslinker with various non-vinyl crosslinkers. In all of the examples 200 ppm of sodium chlorate was added to the polymerization mixture prior to polymerization. Examples 31 and 32 were controls with only vinyl crosslinker. Examples 33-35 used polyethylene glycol (PEG) 600 as non-vinyl agent. Examples 36-39 used PEG of various molecular weights. Examples 40-43 used as the non-vinyl agent: glycerin, ethylene glycol diglycidyl ether (EGDGE), hexane diamine (HexDAm), and ethylene glycol diacetate (EGDAc). The values given are all for the heat-treated samples. (Resin Preparation Procedure 1. Heat-Treatment Procedure 3.)

TABLE 6

Use of Non-Vinyl Crosslinkers With HE-TMPTA

| Ex. No. | HE-TMPTA (ppm) | Non-Vinyl (ppm) | CC (g/g) | 0.6 AUL (g/g) | 0.9 AUL (g/g) | % Ext |
|---|---|---|---|---|---|---|
| 31 | 5500 | None | 30.0 | 26.5 | 19.0 | 6.1 |
| 32 | 3000 | None | 35.4 | 20.9 | 12.8 | ND |
| 33 | 3000 | PEG 600 3000 | 31.3 | 27.2 | 23.1 | 4.8 |
| 34 | 4000 | PEG 600 2000 | 29.7 | 26.8 | 23.7 | 9.5 |
| 35 | 2000 | PEG 600 4000 | 30.6 | 26.7 | 21.5 | 5.8 |
| 36 | 3000 | PEG 200 600 | 28.9 | 25.7 | 20.2 | 5.3 |
| 37 | 3000 | PEG 400 2000 | 29.0 | 25.6 | 24.2 | 6.8 |
| 38 | 3000 | PEG 1000 5000 | 30.3 | 27.0 | 23.4 | 9.4 |
| 39 | 3000 | PEG 3400 5000 | 32.0 | 26.3 | 14.8 | 5.5 |
| 40 | 3000 | Glycerin | 30.1 | 26.5 | 17.0 | 6.8 |

TABLE 6-continued

Use of Non-Vinyl Crosslinkers With HE-TMPTA

| Ex. No. | HE-TMPTA (ppm) | Non-Vinyl (ppm) | CC (g/g) | 0.6 AUL (g/g) | 0.9 AUL (g/g) | % Ext |
|---|---|---|---|---|---|---|
| 41 | 3000 | 150 EGDGE | 30.7 | 26.4 | 16.6 | 5.3 |
| 42 | 3000 | 400 HexDAm | 29.7 | 25.4 | 20.3 | 6.5 |
| 43 | 3000 | 225 EGDAc | 30.1 | 25.4 | 21.3 | 10.3 |
|    |      | 1000 |      |      |      |     |

EXAMPLES 44-50

Use of TMPTA or AMA Vinyl Crosslinker with PEG 600 Non-Vinyl Crosslinker—Table 7

These examples used a blend of either TMPTA or allylmethacrylate (AMA) as vinyl crosslinker with PEG 600 as non-vinyl crosslinker. In all of the examples, 200 ppm of sodium chlorate was added to the polymerization mixture prior to polymerization. Examples 44 and 47 were controls with only TMPTA (No. 44) or AMA (No. 47) as crosslinker. Examples 45-46 contained blends of TMPTA and PEG, while examples 48-50 contained blends of AMA and PEG. The values given are all for the heat-treated samples. (Resin Preparation Procedure 1. Heat-Treatment Procedure 3.)

TABLE 7

Use of TMPTA or AMA Vinyl Crosslinker With PEG 600 Non-Vinyl Crosslinker

| Ex. No. | Vinyl X-L (ppm) | PEG 600 (ppm) | CC (g/g) | 0.6 AUL (g/g) | 0.9 AUL (g/g) | % Ext |
|---|---|---|---|---|---|---|
| 44 | TMPTA 1500 | None | 35.4 | 12.8 | 8.1 | ND |
| 45 | TMPTA 1500 | 2000 | 30.0 | 26.0 | 20.9 | 5.6 |
| 46 | TMPTA 2000 | 1000 | 29.2 | 23.0 | 17.1 | 5.4 |
| 47 | AMA 6000 | None | 34.5 | 18.7 | 9.6 | 6.0 |
| 48 | AMA 4000 | 2000 | 31.5 | 27.0 | 19.3 | 4.4 |
| 49 | AMA 6000 | 2000 | 28.6 | 26.2 | 21.0 | 2.3 |
| 50 | AMA 1000 | 8000 | 32.9 | 27.9 | 22.8 | 5.7 |

Use of Dimodal Crosslinkers With HE-TMPTA—Table 8

These examples used a blend of HE-TMPTA (SARTOMER® 9035) vinyl crosslinker with various dimodal crosslinkers. In all of the examples 200 ppm of sodium chlorate was added to the polymerization mixture prior to polymerization. Examples 51 and 52 were controls with only HE-TMPTA as crosslinker. The dimodal agents used were: hydroxyethyl methacrylate (HEMA), polyethylene glycol 400 monomethacrylate (PEG 400 MMA), glycidyl methacrylate (GMA), and allyl glycidyl ether (AGE). The values given are all for the heat-treated samples. (Resin Preparation Procedure 1. Heat-Treatment Procedure 3.)

TABLE 8

Use of Dimodal Crosslinkers With HE-TMPTA

| Ex. No. | Vinyl (ppm) | Dimodal (ppm) | CC (g/g) | 0.6 AUL (g/g) | 0.9 AUL (g/g) | % Ext |
|---|---|---|---|---|---|---|
| 51 | 5500 | 0 | 30.0 | 26.5 | 19.0 | 6.1 |
| 52 | 3000 | 0 | 35.4 | 20.9 | 12.8 | ND |
| 53 | 3000 | HEMA (500) | 28.6 | 26.2 | 21.9 | 7.4 |
| 54 | 3000 | PEG 400 MMA (1000) | 30.8 | 25.4 | 18.9 | 5.7 |
| 55 | 3000 | GMA (300) | 30.8 | 25.7 | 18.5 | 7.6 |
| 56 | 3000 | AGE (500) | 28.2 | 26.0 | 20.3 | 3.9 |

EXAMPLES 57-64

Effect of Heat-Treatment Temperature—Table 9

Examples 57-64 demonstrate the effect of the temperature (HT Temp) of the heat-treatment on final product properties. The water-absorbent resins were prepared with ppm HE-TMPTA (SARTOMER® 9035) and 305 ppm of potassium chlorate in the polymerization mixture. Residence time during heat-treatment at the designated temperature was 20 minutes. Example 57 was the feed for the study. All other values given are for heat-treated samples. (Resin Preparation Procedure 2. Heat-Treatment Procedure 2.)

TABLE 9

Effect of Heat-Treatment Temperature

| Ex. No. | HT Temp (°C.) | 0.3 AUL (g/g) | 0.6 AUL (g/g) | CC (g/g) | % Ext | Res AA (ppm) |
|---|---|---|---|---|---|---|
| 57 | Feed | 14.5 | ND | 35.7 | 11.8 | 308 |
| 58 | 170 | 27.2 | ND | 37.3 | 10.0 | 511 |
| 59 | 180 | 29.5 | ND | 36.4 | 9.5 | 533 |
| 60 | 190 | 32.3 | ND | 34.9 | 7.9 | 473 |
| 61 | 200 | 32.9 | 19.9 | 35.0 | 8.2 | 477 |
| 62 | 210 | 31.7 | ND | 33.5 | 9.2 | 329 |
| 63 | 220 | 31.2 | 22.7 | 35.9 | 11.0 | 338 |
| 64 | 230 | 31.5 | 26.3 | 34.0 | 11.9 | 263 |

These examples demonstrate that high heat-treatment temperatures are necessary in order to achieve both high AUL values and low residual monomer levels. However, the temperatures used are lower than those described in GB Patent Application No. 9208449.0 and used therein to achieve high AUL values.

EXAMPLES 65-77

Effect of Heat-Treatment Time—Table 10

The effect of heat-treatment time on the properties of the resin particles is shown in these examples. Residence time 0 means the time at which the thermometer in the fluid bed indicates a temperature not more than 2° C. below the target temperature. The time period from the time the sample was placed in the heater to reaching residence time 0 generally was about 10 minutes.

Individual samples were heated for various times at 200° C. and 230° C. The crosslinker was HE-TMPTA (SARTOM ER® 9035), and was present at a concentration of 8700 ppm. Potassium chlorate was added to the monomer mixture at a concentration of 305 ppm. (Resin Preparation Procedure 2. Heat-Treatment Procedure 2.)

TABLE 10

Effect of Heat-Treatment Time

| Ex. No. | Temp (°C.) | Time (min) | 0.3 AUL (g/g) | 0.6 AUL (g/g) | CC (g/g) | % Ext. | Res AA (ppm) |
|---|---|---|---|---|---|---|---|
| 65 | Feed | Feed | 15.0 | ND | 33.8 | 12.0 | 349 |
| 66 | 200 | 5 | 29.2 | 16.1 | 33.6 | 10.4 | 409 |
| 67 | 200 | 10 | 29.9 | 21.4 | 33.5 | 9.5 | 365 |
| 68 | 200 | 20 | 30.4 | 23.8 | 31.7 | 8.8 | 408 |
| 69 | 200 | 30 | 28.9 | 24.0 | 30.5 | 8.3 | 388 |
| 70 | 200 | 40 | 28.9 | 24.2 | 30.1 | 8.2 | 362 |
| 71 | 200 | 60 | 27.5 | 24.8 | 29.0 | 8.6 | 355 |
| 72 | 230 | 5 | 31.5 | 24.0 | 33.2 | 9.4 | 350 |
| 73 | 230 | 10 | 30.9 | 23.1 | 31.8 | 9.2 | 320 |
| 74 | 230 | 20 | 31.0 | 24.8 | 32.0 | 9.1 | 308 |
| 75 | 230 | 30 | 30.1 | 25.2 | 31.8 | 8.9 | 302 |
| 76 | 230 | 40 | 29.7 | 24.9 | 30.1 | 8.5 | 305 |
| 77 | 230 | 60 | 28.9 | 24.6 | 29.5 | 9.0 | 285 |

These examples demonstrate that at higher temperatures improvements in AUL values are achieved at shorter heating times. The residual monomer levels decreased with increasing residence time at both temperature levels, but the overall decrease is greater at the higher temperature.

EXAMPLES 78–86

Effect of Chlorate Level—Table 11

Examples 78–86 demonstrate the effect of different potassium chlorate concentrations at a given crosslinker level. The crosslinker is HE-TMPTA (SARTOM ER® 9035), and is used at a concentration of 5000 ppm. The concentration of potassium chlorate in the monomer mix is varied from 0 to 800 ppm, based on acrylic acid. Heat-treatment is performed at 200° C. for 20 minutes residence time (that is, after reaching 200° C.). (Resin Preparation Procedure 3. Heat-Treatment Procedure 2.)

TABLE 11

Effect of Chlorate Level

| Ex. No. | KClO3 (ppm) | 0.3 AUL (g/g) | 0.6 AUL (g/g) | CC (g/g) | % Ext. | Res AA (ppm) |
|---|---|---|---|---|---|---|
| 78 | 0 | 25.9 | 24.1 | 25.5 | 4.7 | 835 |
| 79 | 100 | 29.8 | 25.9 | 30.4 | 7.1 | 465 |
| 80 | 200 | 32.4 | 25.7 | 35.1 | 8.4 | 350 |
| 81 | 300 | 32.8 | 27.1 | 35.3 | 10.1 | 375 |
| 82 | 400 | 34.2 | 26.0 | 38.3 | 12.6 | 317 |
| 83 | 500 | 35.2 | 21.7 | 42.2 | 15.9 | 348 |
| 84 | 600 | 31.1 | 21.4 | 40.0 | 20.8 | 329 |
| 85 | 700 | 31.4 | 18.9 | 42.5 | 21.4 | 296 |
| 86 | 800 | 31.9 | 18.0 | 43.6 | 25.3 | 276 |

These examples demonstrate that an optimum combination of absorption properties and low residual monomer levels is achieved with chlorate concentrations in the range of 200 to 300 ppm of potassium chlorate (based on acrylic acid). Lower levels do not reduce the residual monomer level enough, while higher levels give too great an increase in the percentage of extractable materials.

EXAMPLES 87–94

Effect of Various Oxidizing Agents—Table 12

Examples 87–94 demonstrate the effect of various oxidizing agents. The polymers were prepared using HE-TMPTA (SARTOM ER® 9035). The selected oxidizing agents were added to the monomer mix prior to polymerization. The molar amounts of the added agents were equivalent to 400 ppm of potassium chlorate, (based on acrylic acid). The 30–50 mesh cut of the initial materials are post treated at 220° C. for 20 minutes (after reaching the target temperature). (Resin Preparation Procedure 3. Heat-Treatment Procedure 2.)

TABLE 12

Effect of Various Oxidizing Agents

| | | | Properties | Before Heat-Treatment | | | |
| | | | | After Heat-Treatment | | | |

| Ex. No. | Oxidiz. Agent | Conc. (ppm) | 0.3 psi AUL (g/g) | 0.6 psi AUL (g/g) | CC (g/g) | Ext (%) | Res AA (ppm) |
|---|---|---|---|---|---|---|---|
| 87 | Control | 0 | 8.3 | 7.6 | 42.0 | 11.3 | 379 |
| | | | 29.1 | 15.7 | 34.4 | 8.3 | 624 |
| 88 | KClO3 | 400 | 11.3 | 9.0 | 37.2 | 8.9 | 195 |
| | | | 33.2 | 13.3 | 44.3 | 17.3 | 237 |
| 89 | KBrO3 | 545 | 11.3 | 7.6 | 37.1 | 11.2 | 186 |
| | | | 26.0 | 13.1 | 37.9 | 14.8 | 459 |
| 90 | KIO3 | 700 | 12.6 | 8.3 | 34.2 | 13.4 | ND |
| | | | 26.3 | 20.9 | 32.6 | 12.8 | ND |
| 91 | KNO3 | 330 | 10.0 | 7.8 | 38.0 | 12.0 | ND |
| | | | 27.6 | 20.1 | 29.7 | 7.5 | ND |
| 92 | NaClO4.H2O | 460 | 11.6 | 9.0 | 38.6 | 8.5 | 321 |
| | | | 28.8 | 24.8 | 29.5 | 5.3 | 691 |
| 93 | NaClO2 | 295 | 10.3 | 8.3 | 39.6 | 11.1 | 349 |
| | | | 31.0 | 22.2 | 35.6 | 8.3 | 650 |
| 94 | NaClO.2.5 H2O | 390 | 8.6 | 8.7 | 41.4 | 14.8 | 317 |
| | | | 28.8 | 17.7 | 35.5 | 11.5 | 576 |

The control, containing no oxidizing agent (No. 87), showed a large decrease in capacity after heat-treatment.

Polymer prepared with potassium chlorate, however, increased greatly in centrifuged absorption capacity after heat-treatment, demonstrating the chlorate effect of the current invention. The centrifuged absorption capacity of polymer prepared with potassium bromate increased slightly after heat-treatment, showing that bromates are also effective as the oxidizers of this invention. With potassium iodate the centrifuged absorption capacity of the polymer dropped after heat-treatment, showing limited efficacy in the invention. Potassium nitrate had no effect on product properties compared with the control. The oxidants most effective at producing the "chlorate effect" of the invention were therefore chlorates, chlorites and bromates.

EXAMPLES 95–98

Effect of Moisture Level on Residual

Monomer Level—Table 13

These examples show how the magnitude of the "chlorate effect" on reduction in residual monomer level (Res AA) depends on the moisture content of the resin after drying and comminution, but before heat-treatment. Two resin samples were prepared using HE-TMPTA (SARTOMER® 9035) as crosslinker: (A) a control sample containing no oxidizing agent; (B) a sample of the current invention prepared with 200 ppm of sodium chlorate in the reaction mixture. The average moisture level after initial drying for the two samples was 4.6 percent. Examples 95 A, B show the Res AA levels before any treatment, at which point there was little difference between the samples. Examples 96 A and B are the Res AA levels after a typical heat-treatment (220° C. for 40 minutes), after which the Res AA of the (B) sample of the present invention was 661 ppm less than the (A) sample without oxidizing agent, which is a "chlorate effect" reduction (Delta)in Res AA level of 661 ppm. For Examples 97 A and B, the resins were first reduced in moisture by an average of 7.3 percent by placing the ground resins in a 150° C oven for 16 hours, followed by normal heat-treatment. For Examples 98 A and B, the resins were first reduced in moisture by an average of 8.4 percent by placing the ground resins in a 170° C. oven for 16 h, followed by normal heat-treatment. (Resin Preparation Procedure 1. Heat-Treatment Procedure 1.)

TABLE 13

Effect Of Moisture Level On Residual Monomer Level

| | | Residual Monomer (ppm) | | |
|---|---|---|---|---|
| Ex. No. | Treatment | (A) Without Chlorate | (B) With Chlorate | Delta |
| 95 | None | 473 | 398 | 75 |
| 96 | HT | 1157 | 496 | 661 |
| 97 | 150° C., 16 hr (−7.3% H₂O); HT | 1184 | 931 | 253 |
| 98 | 170° C., 16 hr (−8.4% H₂O); HT | 1210 | 1033 | 177 |

Examples 97 A, B had 7.3 percent less moisture content than Example 96, and the Res AA Delta was reduced from 661 ppm to 253 ppm. Examples 98 A and B had 8.4 percent less moisture content than Example 96, and the Res AA Delta was further reduced from 661 ppm to just 177. As the moisture content of the resins was reduced, the difference between the heat-treated Res AA level of the polymer of this invention (B) and the non-chlorate control (A) decreased. The level of the "chlorate effect" on reduction in residual monomer level therefore depends on the moisture content of the resin after drying but before heat-treatment. Greater moisture levels lead to a greater "chlorate effect", and therefore lower residual monomer levels.

EXAMPLES 99–101

Effect of Moisture Level on

Absorption Properties—Table 14

These examples show how the "chlorate effect", as it relates to absorption properties, depends on the moisture content of the resin after drying and sizing but before heat-treatment. Examples 99–101 were all produced from a single batch of resin using HE-TMPTA (SARTOMER® 9035) as crosslinker, where 250 ppm of potassium chlorate was added to the polymerization mixture, and 7.0 weight percent (based on total solids) of fines material (from an equivalent earlier polymerization) was added to the reaction mixture. The three samples, with 10.9 percent, 3.7 percent, and 1.8 percent moisture after drying, were prepared by controlled drying of the single batch followed by sizing and heat-treatment. (Resin Preparation Procedure 4. Heat-Treatment Procedure 1.)

TABLE 14

Effect Of Moisture Level On Absorption Properties

| | | Example No. (% Moisture) | | |
|---|---|---|---|---|
| Property | | 99 (10.9%) | 100 (3.7%) | 101 (1.8%) |
| 2.1 kPa AUL (g/g) | Before HT | 15.7 | 15.7 | 15.9 |
| | After HT | 31.1 | 29.9 | 29.2 |
| 4.1 kPa AUL (g/g) | Before HT | 8.9 | 9.2 | 9.2 |
| | After HT | 23.5 | 23.6 | 23.5 |
| CC (g/g) | Before HT | 29.7 | 33.3 | 34.8 |
| | After HT | 31.8 | 30.6 | 29.3 |

There was little difference in the 4.1 kPa (0.6 psi) AUL values between the samples, but a strong difference in heat-treated centrifuged absorption capacity values. Higher moisture levels before heat-treatment gave higher centrifuged absorption capacities after heat-treatment. In other words, the "chlorate effect" to give greater post heat-treatment centrifuged absorption capacities is itself greater when there have been higher moisture levels prior to heat-treatment.

EXAMPLES 102–103

Surface Treatment of Hydrogel with

Oxidizer—Table 15

Examples 102–103 demonstrate an alternate method of uniformly applying the oxidizer of the present invention. For these examples a hydrogel sample was prepared using 4000 ppm HE-TMPTA (SARTOMER® 9035) as crosslinker but without addition of any oxidizing agent to the reaction. After reaction, one half of the hydrogel was dried, sized, and heat-treated to give Example 99. Of the remaining hydrogel, 300 g were spread evenly on a nylon mesh screen and sprayed with 24 g of aqueous 0.1 percent potassium chlorate solution, or the equivalent of 300 ppm potassium chlorate based on monomer. This gel was then dried, sized, and heat-treated as in Example 102 to give Example 103. Example 103 therefore shows an alternate embodiment of the present invention, while Example 102 shows a control result obtained when the oxidizing agent of the present invention is omitted. The "chlorate effect" exhibited by Example 103 on both heat-treated capacity and heat-treated residual monomer shows that the oxidizer of the present invention may also be applied by surface treatment to the undried hydrogel after polymerization. (Resin Preparation Procedure 1. Heat-Treatment Procedure 1.)

TABLE 15

Surface Treatment of Hydrogel with Oxidizer

| Ex. No. | ClO$_3$ present | 0.3 psi AUL (g/g) | 0.6 psi AUL (g/g) | CC (g/g) | Ext (%) | Res AA (ppm) |
|---|---|---|---|---|---|---|
| 102 | No | 27.4 | 11.0 | 31.7 | 3.0 | 189 |
|  |  | 24.9 | 22.5 | 24.7 | 2.0 | 660 |
| 103 | Yes | 23.4 | 10.8 | 31.1 | 3.2 | 135 |
|  |  | 29.4 | 24.8 | 29.4 | 4.3 | 435 |

Properties Before Heat-Treatment / After Heat-Treatment

EXAMPLES 104–105

Effect of Recycled Fines on Product Properties—Table 16

Examples 104–105 demonstrate that it is possible to prepare the resin of the current invention with addition of recycled "fines" to the polymerization mixture. "Fines" are the fraction of polymer that passes through a 140 mesh screened when the dried and ground product is screened prior to heat-treatment. The resin of Examples 104–105 was prepared with HE-TMPTA (SARTOMER® 9035) as crosslinker, with 250 ppm of potassium chlorate added to the polymerization mixture prior to polymerization. Example 104 was a control containing no fines. Example 105 had 7.0 weight percent (based on total solids) of fines material from an equivalent earlier polymerization added to the reaction mixture. Comparison of the two runs shows that addition of the fines had essentially no effect on product properties, or on the extent of the "chlorate effect" on either heat-treated residual monomer concentration or heat-treated centrifuged absorption capacity. (Resin Preparation Procedure 4. Heat-Treatment Procedure 1.)

TABLE 16

Effect of Recycled Fines on Product Properties

Properties Before Heat-Treatment / After Heat-Treatment

| Ex. No. | Fines (wt %) | 2.1 kPa AUL (g/g) | 4.1 kPa AUL (g/g) | CC (g/g) | Ext (%) | Res AA (ppm) |
|---|---|---|---|---|---|---|
| 104 | 0 | 20.9 | 9.8 | 36.9 | 8.9 | 566 |
|  |  | 30.5 | 24.9 | 31.1 | 9.8 | 618 |
| 105 | 7.0 | 21.0 | 9.9 | 35.5 | 8.8 | 597 |
|  |  | 29.9 | 24.6 | 29.8 | 7.5 | 618 |

EXAMPLES 106–109

Comparative Analysis of Absorption vs. Load—Table 17

For these examples three representative commercially available water-absorbent resins and three water-absorbent resins of the current invention were examined to demonstrate that the resins of the current invention exhibit consistently high centrifuged absorption capacity at increasingly higher loads as compared to commercially available water-absorbent resins. The samples were measured for centrifuged capacity and AUL at 2.1 kPa (0.3 psi), 4.1 kPa (0.6psi), 5.5 kPa (0.8 psi) and 6.9 kPa (1.0 psi). loads. The soak time for the absorption under load tests was 60 minutes. The commercially available water-absorbent resins were Example 106, DRYTECH" 2000 (trademark of The Dow Chemical Company); Example 107, Stockhausen SXM™ 100; Example 108, Hoechst IM™ 3400. The water-absorbent resins of the current invention were Examples 21 and 23 from before, and Example 109, which was prepared according to Resin Preparation Procedure 2 with 200 ppm of potassium chlorate, 8000 ppm of HE-TMPTA (SARTOMER® 9035), and heat-treated at 230° C. for 10 minutes using Heat-Treatment Procedure 2.

TABLE 17

Comparative Analysis of Absorption vs. Load

| Ex. No. | Source | CC (g/g) | AUL 0.3 psi | AUL 0.6 psi | AUL 0.8 psi | AUL 1.0 psi |
|---|---|---|---|---|---|---|
| 106 | DRYTECH™ 2000 | 29.2 | 18.9 | 9.2 | 8.7 | 8.0 |
| 107 | Stockhausen™ SXM 100 | 39.0. | 32.9 | 21.1 | 15.8 | 12.1 |
| 108 | Hoechst IM™ 3400 | 28.4 | 21.5 | 7.9 | 7.3 | 6.9 |
| 21 | This Invention | 31.7 | 31.6 | 26.4 | 23.0 | 15.0 |
| 23 | This Invention | 38.6 | 32.8 | 25.7 | 17.8 | 9.1 |
| 109 | This Invention | 27.4 | 27.9 | 25.3 | 22.9 | 22.0 |

What is claimed is:

1. A water-absorbent resin particle comprising: from 80 to 99.9 weight percent of a crosslinked carboxyl-containing polymer prepared by polymerizing a polymerization mixture which comprises:

(a) from 70 to 99.9 weight percent of one or more ethylenically unsaturated carboxyl containing monomers, (b) from 0.1 to 5 weight percent of one or more crosslinking agents, and (c) from 0 to 25 weight percent of one or more comonomers copolymerizable with the carboxyl containing monomer, (d) from 10 to 2000 ppm by weight of a chlorine or bromine containing oxidizing agent, wherein the weight percentages and ppm of the polymerization mixture are based on the total weight of (a), (b) and (c), wherein the oxidizing agent has been substantially uniformly distributed within the resin particle prior to heat-treatment, and wherein the resin particle has been heated at a temperature of from 170° C. to 250° C. for from 1 to 60 minutes.

2. The water-absorbent resin particle of claim 1, wherein the carboxyl containing monomer is one or more ethylenically unsaturated carboxylic acids, ethylenically unsaturated carboxylic acid anhydrides or a salt thereof; the optional comonomer is selected from the group consisting of an acrylamide, a vinyl pyrrolidone, a vinyl sulphonic acid or a salt thereof, an acrylonitrile, a cellulosic monomer, a modified cellulosic monomer, a polyvinyl alcohol monomer and a starch hydrolyzate monomer; and the crosslinking agent is one or more polyvinyl crosslinking agents, or one or more polyvinyl crosslinking agents and one or more non-vinyl crosslinking agents, or one or more polyvinyl crosslinking agents and one or more dimodal crosslinking agents.

3. The water-absorbent resin particle of claim 1 or 2, wherein the water-absorbent resin particle has a centrifuged absorption capacity of 26 g/g or greater and an absorption under load of 24 g/g or greater at 4.1 kPa (0.6 psi) load, or (i) the resin particle has a centrifuged absorption capacity of 26 g/g or greater and an absorption under load of 17 g/g or greater at 5.5 kPa (0.8 psi) load, or (ii) the resin particle has a centrifuged absorption capacity of 26 g/g or greater and an absorption under load of 14 g/g or greater at 6.9 kPa (1 psi) load, or (iii) the resin particle has an absorption under load of 22 g/g or greater at 5.5 kPa (0.8 psi) load and the resin particle has an absorption under load of 20 g/g or greater at 6.9 kPa (1 psi) load, or (iv) the resin particle has a centrifuged absorption capacity of 30 g/g or greater and an absorption under load of 24 g/g or greater at 4.1 kPa (0.6 psi) load, or (v) the resin particle has a centrifuged absorption capacity of 30 g/g or greater and an absorption under load of 17 g/g or greater at 5.5 kPa (0.8 psi) load, or (vi) the resin particle has a centrifuged absorption capacity of 30 g/g or greater and an absorption under load of 14 g/g or greater at 6.9 kPa (1 psi) load, or (vii) the resin particle has a centrifuged absorption capacity of 30 g/g or greater and an absorption under load of 22 g/g or greater at 5.5 kPa (0.8 psi) load, or (viii) the resin particle has a centrifuged absorption capacity of 37 g/g or greater and an absorption under load of 17 g/g or greater at 5.5 kPa (0.8 psi) load.

4. The water-absorbent particle of claim 3, wherein the polyvinyl crosslinking agent is a di- or polyester of an unsaturated mono- or polycarboxylic acid with a polyol, an unsaturated polyester obtained by reacting a polyol with an unsaturated acid, a di- or tri(meth)acrylic acid ester obtained by reacting a polyepoxide with a (meth)acrylic acid, a bis(meth)acrylamide, a carbamyl ester obtained by reacting a polyisocyanate with a hydroxyl group-containing monomer, a di- or poly(meth)allyl ether of a polyol, a di- or poly-allyl ester of a polycarboxylic acid, an ester of an unsaturated mono- or polycarboxylic acid with a mono (meth)allyl ester of a polyol; an ethylenically unsaturated compound containing at least one group reactive with carboxyl, carboxylic acid anhydride, hydroxyl, amino or amide groups; or an oxide, hydroxide or weak acid salt of an alkaline earth metal or zinc.

5. The water-absorbent particle of 4, wherein the polyvinyl crosslinking agent employed is a compound of the formula

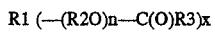

wherein

R1 is a straight- or branched-chain polyalkoxy radical with 1 to 10 carbon atoms, optionally substituted with one or more oxygen atoms in the backbone, having x valences;

R2 is independently in each occurrence an alkylene group of 2 to 4 carbon atoms;

R3 is independently in each occurrence a straight- or branched-chain alkenyl moiety with 2 to 10 carbon atoms;

n is a positive integer from 1 to 20;

x is a positive integer from 2 to 8.

6. The water-absorbent particle of claim 5 wherein R1 is derived from trimethylolpropane, R2 is ethylene (—CH$_2$CH$_2$—), R3 is vinyl (—CH=CH$_2$), n is an average of from 2 to 6, and x is 3.

7. The water-absorbent particle of claims 6 wherein the carboxyl-containing monomer is a polymer of acrylic or methacrylic acid or a salt thereof, and the oxidizing agent is sodium chlorate, potassium chlorate, sodium bromate, potassium bromate, sodium chlorite or potassium chlorite, and the particle has been heated at a temperature of from 200° C. to 235° C. for from 5 to 40 minutes.

8. An absorbent structure comprising a woven or nonwoven structure of paper, synthetic fibers, or natural fibers and water-absorbent resin particles of any of claims 1 or 2.

9. A process for the preparation of water-absorbent resin particles which comprises:

(I) polymerizing a polymerization mixture comprising:
  (a) from 70 to 99.9 weight percent of one or more ethylenically unsaturated carboxyl containing monomers,
  (b) from 0.1 to 5 weight percent of one or more crosslinking agents,
  (c) from 0 to 25 weight percent of one or more comonomers copolymerizable with the carboxyl containing monomer,
  (d) an aqueous or nonaqueous polymerization medium, and
  (e) from 10 to 2000 ppm by weight of a chlorine or bromine containing oxidizing agent to form a crosslinked hydrogel wherein the weight percentages and ppm are based on the total weight of (a), (b) and (c);

(II) optionally, comminuting the hydrogel to particles;

(III) drying the hydrogel by substantially removing the polymerization medium to form resin;

(IV) optionally, comminuting the resin to particles;

(V) heating the particles at a temperature of from 170° C. to 250° C. for from 1 to 60 minutes.

10. A process for the preparation of water-absorbent resin particles which comprises:

(I) polymerizing a polymerization mixture comprising:
  (a) from 70 to 99.9 weight percent of one or more ethylenically unsaturated carboxyl containing monomers,
  (b) from 0.1 to 5 weight percent of one or more crosslinking agents,
  (c) from 0 to 25 weight percent of one or more comonomers copolymerizable with the carboxyl containing monomer, and
  (d) an aqueous or nonaqueous polymerization medium to form a crosslinked hydrogel wherein the weight percentages are based on the total weight of (a), (b) and (c);

(II) optionally, comminuting the hydrogel to particles;

(III) applying to the hydrogel a chlorine or bromine containing oxidizing agent dispersed or dissolved in a liquid so that there is substantially uniformly distributed through the hydrogel particles from 10 to 2000 ppm by weight, based on the weight of (a), (b) and (c), of the chlorine or bromine containing oxidizing agent (IV) drying the hydrogel by substantially removing the polymerization medium and the liquid to form resin;

(V) optionally, comminuting the resin particles;

(VI) heating the particles at a temperature of from 170° C. to 250° C. for from 1 to 60 minutes.

11. The process of claim 9 or claim 10, wherein the carboxyl containing monomer is one or more ethylenically unsaturated carboxylic acids, ethylenically unsaturated carboxylic acid anhydrides or a salt thereof; the optional comonomer is selected from the group consisting of an acrylamide, a vinyl pyrrolidone, a vinyl sulphonic acid or a salt thereof, an acrylonitrile, a cellulosic monomer, a modified cellulosic monomer, a polyvinyl alcohol monomer and a starch hydrolyzate monomer; and the crosslinking agent is one or more polyvinyl crosslinking agents, or one or more polyvinyl crosslinking agents and one or more non-vinyl crosslinking agents, or one or more polyvinyl crosslinking agents and one or more dimodal crosslinking agents.

12. The process of claim 11, wherein the water-absorbent resin particles have a centrifuged absorption capacity of 26 g/g or greater and an absorption under load of 24 g/g or greater at 4.1 kPa (0.6 psi) load, or (i) the resin particles have a centrifuged absorption capacity of 26 g/g or greater and an absorption under load of 17 g/g or greater at 5.5 kPa (0.8 psi) load, or (ii) the resin particles have a centrifuged absorption capacity of 26 g/g or greater and an absorption under load of 14 g/g or greater at 6.9 kPa (1 psi) load, or (iii) the resin particles have an absorption under load of 22 g/g or greater at 5.5 kPa (0.8 psi) load and the resin particle has an absorption under load of 20 g/g or greater at 6.9 kPa (1 psi) load, or (iv) the resin particles have a centrifuged absorption capacity of 30 g/g or greater and an absorption under load of 24 g/g or greater at 4.1 kPa (0.6 psi) load, or (v) the resin particles have a centrifuged absorption capacity of 30 g/g or greater and an absorption under load of 17 g/g or greater at 5.5 kPa (0.8 psi) load, or (vi) the resin particles have a centrifuged absorption capacity of 30 g/g or greater and an absorption under load of 14 g/g or greater at 6.9 kPa (1 psi) load, or (vii) the resin particles have a centrifuged absorption capacity of 30 g/g or greater and an absorption under load of 22 g/g or greater at 5.5 kPa (0.8 psi) load, or (viii) the resin particles have a centrifuged absorption capacity of 37 g/g or greater and an absorption under load of 17 g/g or greater at 5.5 kPa (0.8 psi) load.

13. The process of claim 12, wherein the polyvinyl crosslinking agent is a di- or polyester of an unsaturated mono- or polycarboxylic acid with a polyol, and unsaturated polyester obtained by reacting a polyol with an unsaturated acid, a di- or tri(meth)acrylic acid ester obtained by reacting a polyepoxide with a (meth)acrylic acid, a bis(meth)acrylamide, a carbamyl ester obtained by reacting a polyisocyanate with a hydroxyl group-containing monomer, a di- or poly(meth)allyl ether of a polyol, a di- or poly-allyl ester of a polycarboxylic acid, an ester of an unsaturated mono- or polycarboxylic acid with a mono(meth)allyl ester of a polyol; an ethylenically unsaturated compound containing at least one group reactive with carboxyl, carboxylic acid anhydride, hydroxyl, amino or amide groups; or an oxide, hydroxide or weak acid salt of an alkaline earth metal or zinc.

14. The process of claim 13 wherein the polyvinyl crosslinking agent employed is a compound of the formula

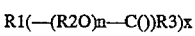

wherein

R1 is a straight- or branched-chain polyalkoxy radical with 1 to 10 carbon atoms, optionally substituted with one or more oxygen atoms in the backbone, having x valences;

R2 is independently in each occurrence an alkylene group of 2 to 4 carbon atoms;

R3 is independently in each occurrence a straight- or branched-chain alkenyl moiety with 2 to 10 carbon atoms;

n is a positive integer from 1 to 20;

x is a positive integer from 2 to 8.

15. The process of claim 14 wherein R1 is derived from trimethylolpropane, R2 is ethylene (—CH$_2$CH$_2$—), R3 is vinyl (—CH=CH$_2$), n is an average of from 2 to 6, and x is 3.

16. The process of claim 15 wherein the carboxyl-containing monomer is a polymer of acrylic or methacrylic acid or a salt thereof, and the oxidizing agent is sodium chlorate, potassium chlorate, sodium bromate, potassium promate, sodium chlorite or potassium chlorite.

17. The process of claim 16 wherein the particles are heated at a temperature of from 200° C. to 235° C. for from 5 to 30 minutes.

18. The process of claim 9 or 10 wherein the only crosslinking agents present are those in the polymerization mixture of (I).

19. Water-absorbent resin particles produced by the process of any of claims 9 or 10.

20. An absorbent structure comprising a woven or nonwoven structure of paper, synthetic fibers, or natural fibers and water-absorbent resin particles of claim 19.

* * * * *

UNITED STATES PATENT AND TRADEMARK OFFICE
CERTIFICATE OF CORRECTION

PATENT NO.   : 5,629,377
DATED        : May 13, 1997
INVENTOR(S)  : Josef H. Burgert et al.

It is certified that error appears in the above-identified patent and that said Letters Patent is hereby corrected as shown below:

Column 33,
Line 9, "claim" should read -- claims --.
Line 55, "4" should read -- Claim 4 --.

Column 34,
Line 10, "claims" should read -- claim --.
Line 16, "5 to40" should read -- 5 to 40 --.

Column 35,
Line 50, "and" should read -- an --.

Column 36,
Line 16, "R1(—(R2O)n—C(_())_R3)x" should read -- R1(—(R2O)n—C(O)R3)x --.
Line 38, "promate" should read -- bromate --.

Signed and Sealed this

Eighteenth Day of December, 2001

Attest:

*Attesting Officer*

JAMES E. ROGAN
*Director of the United States Patent and Trademark Office*